(12) United States Patent
Angermann et al.

(10) Patent No.: US 6,232,271 B1
(45) Date of Patent: May 15, 2001

(54) 1-METHYL-5-ALKYLSULFONYL-, 1-METHYL-5-ALKYLSULFINYL- AND 1-METHYL-5-ALKYLTHIO- SUBSTITUTED PYRAZOLYLPYRAZOLES, PROCESSES FOR THEIR PREPARATION AND THEIR USE AS HERBICIDES

(75) Inventors: Alfred Angermann, Kriftel/Ts. (DE); Helga Franke, Sommerset West (ZA); Rainer Preuss, Hofheim (DE); Uwe Hartfiel, Frankfurt (DE); Holger Wagner, Langgöns-Dornholzhausen (DE); Hermann Bieringer, Eppstein (DE); Thomas Auler, Kelsterbach (DE); Christopher Rosinger, Hofheim (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/196,575

(22) Filed: Nov. 20, 1998

(30) Foreign Application Priority Data

Nov. 24, 1997 (DE) ................................. 197 51 943

(51) Int. Cl.[7] .......................... C07D 405/14; A01N 43/56
(52) U.S. Cl. ........................................ 504/282; 548/365.4
(58) Field of Search .......................... 548/365.4; 504/282

(56) References Cited

U.S. PATENT DOCUMENTS 5,840,912 * 11/1998 Geisler et al. .................. 548/365.4

FOREIGN PATENT DOCUMENTS

| | | |
|---|---|---|
| 19623892 A1 | 12/1997 | (DE) . |
| 0542388 | 5/1993 | (EP) . |
| 0542388 A1 | 5/1993 | (EP) . |
| WO 93/10100 | 5/1993 | (WO) . |
| WO 94/08999 | 4/1994 | (WO) . |
| WO 96/06303 | 3/1996 | (WO) . |
| WO 96/09303 | 3/1996 | (WO) . |
| WO 97/09313 | 3/1997 | (WO) . |

* cited by examiner

Primary Examiner—Robert W. Ramsuer
(74) Attorney, Agent, or Firm—Frommer Lawrence & Haug LLP

(57) ABSTRACT

1-Methyl-5-alkylsulfonyl-, 1-methyl-5-alkylsulfinyl- and 1-methyl-5-alkylthio-substituted pyrazolylpyrazoles, processes for their preparation and their use as herbicides 1-Methyl-5-alkylsulfonyl-, 1-methyl-5-alkylsulfinyl- and 1-methyl-alkylthio-substituted pyrazolylpyrazoles of the formula (I) are described as herbicidally active compounds.

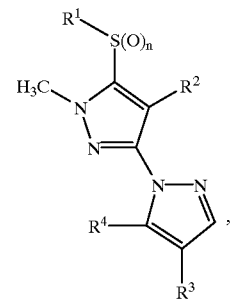

In this formula (I), $R^1$ and $R^4$ are various substituents, $R^2$ is halogen or cyano, $R^3$ is cyano, nitro or thiocarbamoyl and n is 0, 1 or 2.

15 Claims, No Drawings

1-METHYL-5-ALKYLSULFONYL-, 1-METHYL-5-ALKYLSULFINYL- AND 1-METHYL-5-ALKYLTHIO- SUBSTITUTED PYRAZOLYLPYRAZOLES, PROCESSES FOR THEIR PREPARATION AND THEIR USE AS HERBICIDES

1-Methyl-5-alkylsulfonyl-, 1-methyl-5-alkylsulfinyl- and 1-methyl-5-alkylthio-substituted pyrazolylpyrazoles, processes for their preparation and their use as herbicides The invention relates to 1-methyl-5-alkylsulfonyl-, 1-methyl-5-alkylsulfinyl- and 1-methyl-5-alkylthio-substituted pyrazolylpyrazoles, to processes for their preparation and to their use as herbicides.

Herbicidally active pyrazolylpyrazoles are known from various publications. Thus, EP-A 0 542 388, WO 94108999 and WO 96109303 describe pyrazolylpyrazoles which carry hydrogen or optionally halogen-substituted alkyl, alkylthio or alkoxy in position 5. The German patent application No. 196 23 892.7, which has earlier priority but is not prior published, mentions pyrazolylpyrazoles which carry a radical from the group consisting of alkyl, alkylthio, alkylsulfinyl, alkylsulfonyl and alkoxy in position 5, where these radicals are in each case unsubstituted or substituted by halogen. WO 97/09313 discloses pyrazolylpyrazoles which are substituted in the 5-position of one of the pyrazole rings by, inter alia, an unsubstituted or substituted radical from the group consisting of alkyl, alkoxy and alkylthio, and in the 4-position of the other pyrazole ring by the thiocarbamoyl group.

Particular properties of, specifically, 1-methyl-5-alkylsulfonyl-, 1-methyl-5-alkylsulfinyl- and 1-methyl-5-alkylthio-substituted pyrazolylpyrazoles are not disclosed in these publications. Moreover, the herbicidal activity of the compounds mentioned in these publications is not always sufficient, or, if the herbicidal activity is sufficient, there are selectivity problems in crops of useful plants.

It is an object of the present invention to provide pyrazolylpyrazoles having superior biological properties.

This object is achieved by the 1-methyl-5-alkylsulfonyl-, 1-methyl-5-alkylsulfinyl- and 1-methyl-5-alkylthio-substituted pyrazolylpyrazoles of the formula (I)

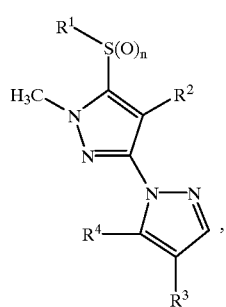

in which $R^1$ is $C_1$–$C_3$-alkyl, $C_3$–$C_8$-cycloalkyl or $C_2$–$C_3$-alkenyl, where these radicals are unsubstituted or substituted by one or more identical or different halogen atoms;

$R^2$ is halogen or cyano;

$R^3$ is cyano, nitro or thiocarbamoyl;

$R^4$ is halogen, $C_1$–$C_6$-alkyl which is unsubstituted or substituted by one or more identical or different halogen atoms, or is one of the groups

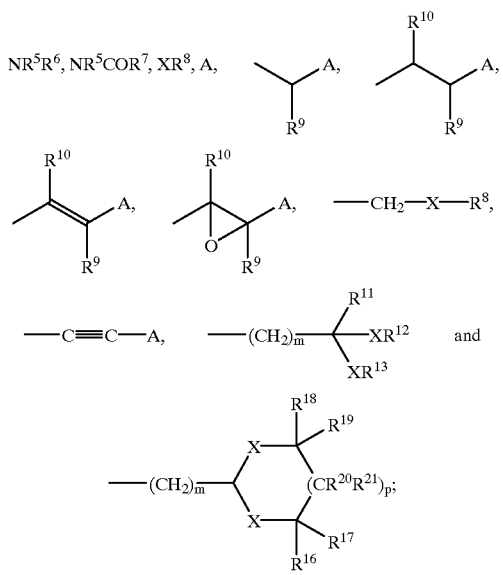

A is cyano or one of the groups

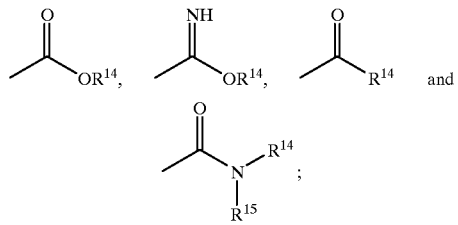

$R^5$ is hydrogen, $C_1$–$C_6$-alkyl, $C_3$–$C_8$-cycloalkyl, $C_2$–$C_6$-alkenyl or $C_2$–$C_6$-alkynyl, where the four last mentioned radicals are unsubstituted or substituted by one or more identical or different halogen atoms;

$R^6$ is $C_1$–$C_6$-alkyl, $C_3$–$C_8$-cycloalkyl, $C_2$–$C_6$-alkenyl or $C_2$–$C_6$-alkynyl, where these four radicals are unsubstituted or substituted by one or more identical or different halogen atoms, di-($C_1$–$C_4$-alkoxy)-$C_1$–$C_3$-alkyl or the group

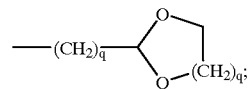

$R^7$ is hydrogen, $C_1$–$C_4$alkyl or $C_3$–$C_8$-cycloalkyl, where the two last-mentioned radicals are unsubstituted or substituted by one or more identical or different halogen atoms;

$R^8$ is $C_1$–$C_6$-alkyl whose carbon chain may be interrupted by one or more identical or different heteroatoms from the group consisting of oxygen and sulfur and which is unsubstituted or substituted by one or more identical or different halogen atoms;

$R^9$ is hydrogen, $C_1$–$C_3$-alkyl, halogen, amino, $C_1$–$C_4$-alkylamino or di-($C_1$–$C_4$-alkyl)amino;

$R^{10}$ is hydrogen, $C_1$–$C_3$-alkyl, halogen, amino, hydroxyl, $C_1$–$C_4$-alkylamino or di-($C_1$–$C_4$-alkyl)amino;

$R^{11}$ is hydrogen, $C_1$–$C_3$-alkyl or the group $XR^{12}$;

$R^{12}$ is $C_1$–$C_6$-alkyl whose carbon chain may be interrupted by one or more identical or different heteroatoms from the group consisting of oxygen and sulfur and which is unsubstituted or substituted by one or more identical or different halogen atoms;

$R^{13}$ is $C_1$–$C_6$-alkyl whose carbon chain may be interrupted by one or more identical or different heteroatoms from the group consisting of oxygen and sulfur and which is unsubstituted or substituted by one or more identical or different halogen atoms;

$R^{14}$ is $C_1$–$C_6$-alkyl, $C_3$–$C_8$-cycloalkyl, $C_2$–$C_6$-alkenyl or $C_2$–$C_6$-alkynyl, where these four radicals are unsubstituted or substituted by one or more identical or different radicals from the group consisting of $C_1$–$C_4$-alkoxy, $C_1$–$C_4$-alkoxycarbonyl, cyano or halogen, and where the carbon chain of these four abovementioned radicals may be interrupted by one or more identical or different heteroatoms from the group consisting of oxygen and sulfur;

$R^{15}$ is $C_1$–$C_6$-alkyl, $C_3$–$C_8$-cycloalkyl, $C_2$–$C_6$-alkenyl or $C_2$–$C_6$-alkynyl, where these four radicals are unsubstituted or substituted by one or more identical or different radicals from the group consisting of $C_1$–$C_4$-alkoxycarbonyl or halogen, and where the carbon chain of these four abovementioned radicals may be interrupted by one or more identical or different heteroatoms from the group consisting of oxygen and sulfur, or $R^{14}$ and $R^{15}$ together with the linking nitrogen atom form a 3-, 5- or 6-membered saturated, partially saturated or maximally unsaturated ring which is unsubstituted or substituted by one or more methyl groups and where one carbon atom may be replaced by an oxygen atom;

$R^{16}$, $R^{17}$, $R^{18}$, $R^{19}$, $R^{20}$ and $R^{21}$ independently of one another are hydrogen, $C_1$–$C_4$-alkyl which is unsubstituted or substituted by one or more identical or different halogen atoms, or two of these radicals together form a bond;

X is oxygen or sulfur;

m is 0, 1 or 2;

n is 0, 1 or 2;

p is 0, 1 or 2 and q is 1 or 2.

The term "halogen" includes fluorine, chlorine, bromine and iodine. Unless stated otherwise, preference is given to chlorine and fluorine.

The term "$C_1$–$C_3$-alkyl" is to be understood as the methyl, ethyl, propyl and isopropyl radical. "$C_1$–$C_6$-Alkyl" is to be understood as an unbranched or branched hydrocarbon radical having 1, 2, 3, 4, 5 or 6 carbon atoms, such as, for example, in addition to the abovementioned radicals the 1-butyl, 2-butyl, 2-methylpropyl, tert-butyl, pentyl, 2-methylbutyl, 1,1-dimethylpropyl and hexyl radical. Alkyl radicals having a different range of numbers of carbon atoms are to be understood analogously.

The term "$C_3$–$C_8$-cycloalkyl" includes cyclopropyl, cyclobutyl, cyclopentyl, cyclohexyl, cycloheptyl and cyclooctyl.

The terms "$C_2$–$C_6$-alkenyl" and "$C_2$–$C_6$-alkynyl" denote a straight-chain or, if possible, a branched hydrocarbon radical having 2, 3, 4, 5 or 6 carbon atoms, where this hydrocarbon radical includes at least one multiple bond, and this multiple bond can be located in any position of the unsaturated radical in question; preferably, it is not located at the carbon atom which is linked with the remaining molecular moiety of the compound of the formula (I). "$C_2$–$C_6$-Alkenyl" thus denotes, for example, the vinyl, allyl, 2-methyl-2-propenyl, 2-butenyl, pentenyl, 2-methylpentenyl and the hexenyl group. "$C_2$–$C_6$-Alkynyl" denotes, for example, the ethynyl, propargyl, 2-methyl-2-propynyl, 2-butynyl, 2-pentynyl and the 2-hexynyl group. Alkenyl radicals and alkynyl radicals having a different range of numbers of carbon atoms are to be understood analogously.

If the carbon chain of an alkyl, alkenyl or alkynyl radical is interrupted by more than one heteroatom, these heteroatoms should not be directly adjacent to each other.

"$C_1$–$C_4$-Alkoxy" is to be understood as an alkoxy group whose hydrocarbon radical has, analogously, the meaning given under the definitions of alkyl. Alkyl radicals in other compound terms such as "$C_1$–$C_4$-alkylamino" are to be understood likewise. In the case of di-($C_1$–$C_4$-alkyl)amino, the two alkyl radicals can be identical or different.

If a radical is multiply substituted, this is to be understood in such a way that at least two and at most all hydrogen atoms of this radical are substituted by identical or different other radicals. The possibilities of combining the various substituents of the formula (I) are to be understood in such a way that the general principles of the synthesis of chemical compounds are to be observed, i.e. that no compounds are to be formed of which the skilled worker knows that they are chemically unstable or impossible.

Depending on the nature and the linkage of the substituents, the compounds of the formula (I) may be present as stereoisomers. If, for example, one or more alkenyl groups are present, diastereomers may occur. If, for example, one or more asymmetric carbon atoms are present, enantiomers and diastereomers may occur. Stereoisomers can be obtained from the mixtures which are obtained in the preparation by customary separation methods, for example by chromatographic separation process. It is also possible to prepare stereoisomers selectively by employing stereoselective reactions using optically active starting materials and/or auxiliaries. The invention thus also relates to all stereoisomers and mixtures thereof which are embraced by the formula (I) but not specifically defined.

More interesting compounds of the formula (I) are those in which $R^1$ is $C_1$–$C_3$-alkyl, $C_3$–$C_8$-cycloalkyl or $C_2$–$C_3$-alkenyl, where these radicals are unsubstituted or substituted by one or more identical or different halogen atoms from the group consisting of chlorine and fluorine and $R^2$ is bromine, chlorine, fluorine or cyano.

Of particular interest are compounds of the formula (I) in which $R^1$ is $C_1$–$C_3$-alkyl or $C_3$–$C_6$-cycloalkyl, which are optionally substituted by one or more identical or different halogen atoms from the group consisting of chlorine and fluorine;

$R^2$ is bromine, chlorine or cyano;

$R^5$ is hydrogen, $C_1$–$C_6$-alkyl, $C_3$–$C_6$-cycloalkyl, $C_2$–$C_4$-alkenyl or $C_2$–$C_4$-alkynyl, where the four last mentioned radicals are unsubstituted or substituted by one or more identical or different halogen atoms;

$R^6$ is $C_1$–$C_6$-alkyl, $C_3$–$C_6$-cycloalkyl, $C_2$–$C_4$-alkenyl or $C_2$–$C_4$-alkynyl, where these four radicals are unsubstituted or substituted by one or more identical or different halogen atoms, is di-($C_1$–$C_4$-alkoxy)-$C_1$–$C_3$-alkyl or the group

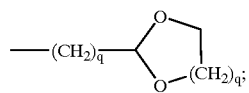

$R^7$ is hydrogen, $C_1$–$C_4$-alkyl or $C_3$–$C_6$-cycloalkyl, where the two last mentioned radicals are unsubstituted or substituted by one or more identical or different halogen atoms;

$R^8$ is $C_1$–$C_6$-alkyl whose carbon chain may be interrupted by a heteroatom from the group consisting of oxygen and sulfur and which is unsubstituted or substituted by one or more identical or different halogen atoms;

$R^{12}$ is $C_1$–$C_6$-alkyl whose carbon chain may be interrupted by a heteroatom from the group consisting of oxygen and sulfur and which is unsubstituted or substituted by one or more identical or different halogen atoms;

$R^{13}$ is $C_1$–$C_6$-alkyl whose carbon chain may be interrupted by a heteroatom from the group consisting of oxygen and sulfur and which is unsubstituted or substituted by one or more identical or different halogen atoms;

$R^{14}$ is $C_1$–$C_6$-alkyl, $C_3$–$C_6$-cycloalkyl, $C_2$–$C_4$-alkenyl or $C_2$–$C_4$-alkynyl, where these four radicals are unsubstituted or substituted by one or more identical or different radicals from the group consisting of $C_1$–$C_4$-alkoxy, $C_1$–$C_4$-alkoxycarbonyl, cyano or halogen, and where the carbon chain of these four abovementioned radicals may be interrupted by a heteroatom from the group consisting of oxygen and sulfur;

$R^{15}$ is $C_1$–$C_6$-alkyl, $C_3$–$C_6$-cycloalkyl, $C_2$–$C_4$-alkenyl or $C_2$–$C_4$-alkynyl, where these four radicals are unsubstituted or substituted by one or more identical or different radicals from the group consisting of $C_1$–$C_4$-alkoxycarbonyl or halogen, and where the carbon chain of these four abovementioned radicals may be interrupted by a heteroatom from the group consisting of oxygen and sulfur, or $R^{14}$ and $R^{15}$ together with the linking nitrogen atom form a 3-, 5- or 6-membered saturated, partially saturated or maximally unsaturated ring which is unsubstituted or substituted by one or more methyl groups and in which one carbon atom may be replaced by an oxygen atom and n is 1 or 2.

Preference is given to compounds of the formula (I) in which $R^1$ is $C_1$–$C_3$-alkyl or $C_3$–$C_6$-cycloalkyl;

$R^8$ is $C_1$–$C_6$-alkyl whose carbon chain may be interrupted by an oxygen atom and which is unsubstituted or substituted by one or more identical or different halogen atoms;

$R^{12}$ is $C_1$–$C_6$-alkyl whose carbon chain may be interrupted by an oxygen atom and which is unsubstituted or substituted by one or more identical or different halogen atoms;

$R^{13}$ is $C_1$–$C_6$-alkyl whose carbon chain may be interrupted by an oxygen atom and which is unsubstituted or substituted by one or more identical or different halogen atoms and n is 2.

Particular preference is given to compounds of the formula (I) in which $R^1$ is methyl, ethyl, propyl, isopropyl or cyclopropyl;

$R^3$ is cyano or nitro and $R^4$ is $C_1$–$C_6$-alkyl which is unsubstituted or substituted by one or more identical or different halogen atoms, or is one of the groups

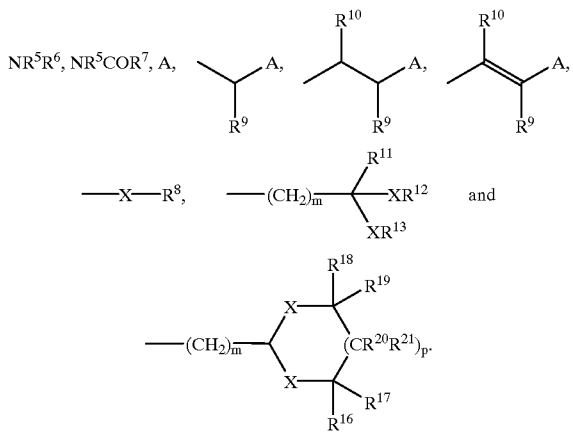

Very particular preference is given to compounds of the formula (I)

in which $R^1$ is methyl or cyclopropyl;

$R^2$ is chlorine or bromine and $R^4$ is one of the groups

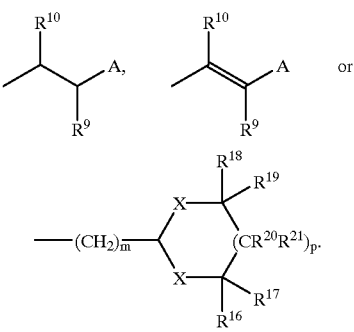

The preparation of the compounds according to the invention is known per se, or it can be carried out analogously by a combination of known processes. Thus, the preparation of the compounds of the formula (I) according to the invention in which n is 0 and $R^4$ is hydrogen, halogen, $NR^5R^6$, $NR^5COR^7$, $XR^8$ or alkyl which is unsubstituted or substituted by one or more identical or different halogen atoms is known from WO 94/08999.

Furthermore, the preparation of the compounds of the formula (I) according to the invention in which n is 0 and $R^4$ is one of the groups

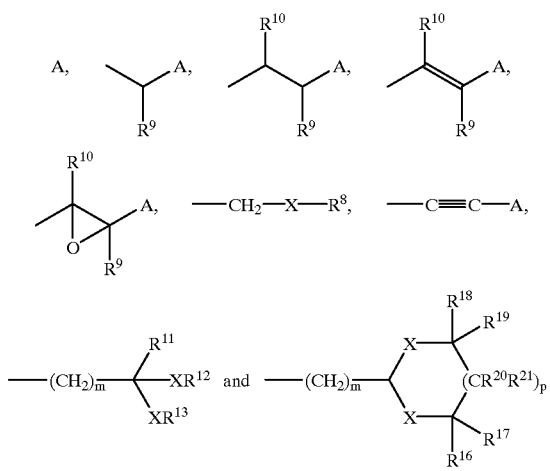

is described in WO 96/09303 and in the German patent application No. 196 23 892.7.

The compounds of the general formula (I) according to the invention in which n is 1 or 2 can be prepared from the corresponding compounds of the formula (I) in which n is 0 by methods known to the person skilled in the art, such as reaction with a suitable oxidizing agent. Suitable oxidizing agents are, for example, hypochlorites, organic peracids, such as m-perchlorobenzoic acid and peracetic acid, inorganic agents, such as Oxone, chlorine, hydrogen peroxide, sodium periodate, sodium perborate, potassium permanganate and atmospheric oxygen.

The novel compounds can be applied in the customary formulations in the form of wettable powders, emulsifiable concentrates, sprayable solutions, dusts or granules. The invention therefore also provides herbicidal and plant growth-regulating compositions comprising compounds of the formula (I).

The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes.

These individual formulation types are known in principle and are described, for example, in Winnacker-Kufchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schdrfeldt, "Grenzfl ächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfonate or else sodium oleoylmethyltaurinate. To prepare the wettable powders, the herbicidal active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8–57.

For further details on the formulation of crop protection products, see for example G. C. Klingman, "Weed Control as a Science", John Wiley and Sons Inc., New York, 1961, pages 81–96 and J. D. Freyer, S. A. Evans, "Weed Control Handbook", 5th Ed., Blackwell Scientific Publications, Oxford, 1968, pages 101–103.

The agrochemical formulations generally contain from 0.1 to 99% by weight, in particular from 0.1 to 95% by weight, of active compound of the formula (I). In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

The compounds of the formula (I) according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is immaterial whether the substances are applied presowing, preemergence or post-emergence. Specifically, examples may be mentioned of some representatives of the monocotyledonous and dicotyledonous weed flora which can be controlled by the compounds according to the invention, without these being a restriction to certain species.

Examples of weed species on which the active compounds act efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active ingredients according to the invention also effect outstanding control of weeds which occur under the specific conditions of rice growing such as, for example, Echinochloa, Sagittaria, Alisma, Eleocharis, Scirpus and Cyperus.

If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledenous weeds, crop plants of economically important crops such as, for example, wheat, barley, rye, rice, corn, sugar beet, cotton and soya, are not damaged at all, or only to a negligible extent. For these reasons, the present compounds are highly suitable for selectively controlling undesired plant growth in plantings for agricultural use or in plantings of ornamentals.

Owing to their herbicidal properties, the active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula (I) according to the invention in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred.

The compounds of the formula (I) can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92111376, WO 92114827, WO 91/19806)

transgenic crop plants which are resistant to certain herbicides of the glufosinate- (cf., for example, EP-A 0 242 236, EP-A 0 242 246) or glyphosate-type (WO 92100377), or of the sulfonylurea-type (EP-A 0 257 993, U.S. Pat. No. 5,013,659)

transgenic crop plants, for example cotton, having the ability to produce *Bacillus thuringiensis* toxins (Bt toxins) which impart resistance to certain pests to the plants (EP-A 0 142 924, EP-A 0 193 259)

transgenic crop plants having a modified fatty acid composition (WO 91/13972)

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423–431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product. To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

The compounds (I) according to the invention can preferably be used in transgenic crops which are resistant to herbicides from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants.

The invention therefore also provides for the use of the compounds (I) according to the invention as herbicides for controlling harmful plants in transgenic crop plants.

The required application rate of the compounds of the formula (I) according to the invention varies with the external conditions, such as temperature, humidity, nature of the herbicide used, etc. It can vary within broad limits, for example between 0.001 and 10.0 kg/ha or more of active substance, but is preferably between 0.005 and 5 kg/ha.

EXAMPLES

A Formulation Examples

A.1 Dusting Agent

A dusting agent is obtained by mixing 10 parts by weight of a compound of the formula (I) and 90 parts by weight of talc as inert substance and comminuting the mixture in a hammer mill.

A.2 Dispersible Powder

A readily water-dispersible wettable powder is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurinate as wefting agent and dispersant and grinding the mixture in a pinned disk mill.

A.3 Dispersion Concentrate

A readily water-dispersible dispersion concentrate is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range, for example, from about 255 to over 277° C.) and grinding the mixture in a ball mill to a fineness below 5 microns.

A.4 Emulsifiable Concentrate

An emulsifiable concentrate is obtained from 15 parts by weight of a compound of the formula (I), 75 parts by weight of cyclohexanone as solvent and 10 parts by weight of ethoxylated monylphenol as emulsifier.

A.5 Water-Dispersible Granules

Water-dispersible granules are obtained by mixing

| 75 parts by weight of a compound of the formula (I), | | |
|---|---|---|
| 10 | " | calcium ligninsulfonate, |
| 5 | " | sodium lauryl sulfate, |
| 3 | " | polyvinyl alcohol and |
| 7 | " | kaolin, | grinding the mixture in a pinned disk mill and granulating the powder in a fluidized bed by spraying on water as granulation liquid.

Water-dispersible granules are also obtained by homogenizing and precomminuting

| 25 parts by weight of a compound of the formula (I), | | |
|---|---|---|
| 5 | " | sodium 2,2'-dinaphthylmethane-6,6'-disulfonate, |
| 2 | " | sodium oleoylmethyltaurinate, |
| 1 | " | polyvinyl alcohol, |
| 17 | " | calcium carbonate and |
| 50 | " | of water | in a colloid mill, followed by grinding in a bead mill, and atomizing and drying the resulting suspension in a spray tower, using a single-substance nozzle.

B. Preparation Examples

B.1 4-Cyano-5-diethoxymethyl-1-(4-chloro-1-methyl-5-methylthio-3-pyrazolyl)pyrazole At −30° C., 2.0 g (6.2 mmol) of 4cyano-5diethoxymethyl-1-(1-methyl-5-methylthio-3-pyrazolyl)pyrazole in 50 ml of methylene chloride are stirred with 0.9 g (6.5 mmol) of sulfuryl chloride for 3 hours. The reaction mixture is subsequently stirred into sodium bicarbonate solution and extracted with methylene chloride and the organic phase is dried (sodium sulfate) and concentrated. Silica gel chromatography of this crude product using ethyl acetate/hexane affords the desired title compound in the form of colorless crystals.

Yield: 1.80 g (81.3% of theory)

Melting point: 129–132° C.

Preparation of the Intermediates a) 3-Amino-4-cyano-1-methyl-5-methylmercaptopyrazole 9.63 g (56.6 mmol) of bis(methylmercapto)methylenemalononitrile are suspended in 50 ml of water and admixed with 3.7 ml (67.9 mmol) of methylhydrazine. The mixture is heated at the boil for 1 hour, the reaction solution is cooled and the precipitate is filtered off with suction and recrystallized from ethanol.

Yield: 6.55 g (68.8% of theory)

Melting point: 120–121° C.

b) 3-Amino-1-methyl-5-methylmercaptopyrazole 5.55 g (33.0 mmol) of 3-amino-4-cyano-1-methyl-5-methylmercaptopyrazole are heated to the boil with 50 ml of 32% strength aqueous sodium hydroxide solution for 24 hours. The reaction mixture is cooled, made slightly acidic with sodium dihydrogen phosphate solution, heated at 50° C. for 8 hours and subsequently extracted with ethyl acetate. The organic phase is dried over sodium sulfate, concentrated and purified by column chromatography (silica gel, hexane/ethyl acetate).

Yield: 1.9 g (39.8% of theory)

c) 3-Hydrazino-1-methyl-5-methylmercaptopyrazole

At 0° C., 1.1 g (15.8 mmol) of sodium nitrite in 4 ml of water are added dropwise to 1.9 g (13.1 mmol) of 3-amino-1-methyl-5-methylmercaptopyrazole in 18 ml of concentrated hydrochloric acid, and the mixture is stirred at 0° C. for 2 hours. At −30° C., a solution of 7.4 ml (32.8 mmol) of tin dichloride hydrate in 5.5 ml of conc. hydrochloric acid is added dropwise, and the mixture is stirred at this temperature for 3 hours. The mixture is then made alkaline using 32% strength aqueous sodium hydroxide solution and extracted with methylene chloride. The organic phase is dried (sodium sulfate) and the solvent is stripped off, giving 2.0 g of product which can be used without any further purification.

d) 4-Cyano-5diethoxymethyl-1-(1-methyl-5-methylthio-3-pyrazolyl)-pyrazole 2.0 g (12.6 mmol) of 3-hydrazino-1-methyl-5-methylmercaptopyrazole and 2.86 g (12.6 mmol) of 2-cyano-4,4-diethoxy-1-(N,N-dimethylamino)-1-buten-3-one in 30 ml of ethanol are heated under reflux for 5 hours. The mixture is then concentrated using a rotary evaporator and the residue is chromatographed over silica gel. This gives 2.50 g (79%) of the desired intermediate as a viscous oil.

B.2 4-Cyano-5diethoxymethyl-1-(4-chloro-1-methyl-5-methylsulfonyl-3-pyrazolyl)pyrazole 1.0 g (2.8 mmol) of 4-cyano-5-diethoxymethyl-1-(4chloro-1-methyl-5-methylthio-3-pyrazolyl)pyrazole (Example B.1) and 1.0 g (5.8 mmol) of m-chloroperbenzoic acid in 10 ml of dichloromethane are stirred at 0° C. for 3 hours and subsequently at room temperature for 12 hours. The reaction mixture is washed with sodium thiosulfate solution, sodium bicarbonate solution and water and dried (sodium sulfate), and the solvent is distilled off. Silica gel column chromatography (ethyl acetate/ hexane) gives the desired product in the form of colorless flakes.

Yield: 0.87 g (80% of theory)

Melting point: 129–132° C.

B.3 4-Cyano-5-(1,3-dioxolan-2-yl)-1-(4chloro-1-methyl-5-methylsulfonyl-3-pyrazolyl)pyrazole 0.6 g (1.5 mmol) of 4-cyano-5-diethoxymethyl-1-(4-chloro-1-methyl-5-methylsulfonyl-3-pyrazolyl)pyrazole (Example B.2) and 0.5 ml of ethylene glycol together with 10 mg of p-toluenesulfonic acid are heated under reflux in 20 ml of toluene for 3 hours. Shaking with sodium bicarbonate and water, drying (sodium sulfate) and concentration using a rotary evaporator gives, in crystalline form, the desired product which can be further purified, if required, by recrystallization or silica gel column chromatography.

Yield: 0.52 g (94% of theory)

Melting point: 154–158° C.

B.4 4-Cyano-5-(1,3-dioxan-2-yl)-1-(4-chloro-1-methyl-5-methylsulfonyl-3-pyrazolyl)pyrazole 1.0 g (3.2 mmol) of 4-cyano-5-formyl-1-(4-chloro-1-methyl-5-methylsulfonyl-3-pyrazolyl)pyrazole, 0.35 g (4.6 mmol) of 1,3-dihydroxypropane and 10 mg of p-toluenesulfonic acid in 40 ml of toluene are heated on a water separator for 3 hours. Work-up as in Example 1.3 gives the title compound in the form of colorless crystals.

Yield: 0.98 g (82.4% of theory)

Melting point: 210–214° C.

Preparation of the Precursor

4-Cyano-5-formyl-1-(4chloro-1-methyl-5-methylsulfonyl-3-pyrazolyl)-pyrazole 1.10 g (3.5 mmol) of 4-cyano-5-diethoxymethyl-1-(4-chloro-1-methyl-5-methylsulfonyl-3-pyrazolyl)pyrazole are dissolved in 20 ml of 1,4-dioxane and, after addition of 2 ml of 50% strength sulfuric acid, heated under reflux for 2 hours. The solution is cooled and the volatile components are then distilled off, and the residue taken up in dichloromethane and extracted with water and sodium bicarbonate solution. Drying with sodium sulfate and concentration using a rotary evaporator gives 0.95 g (86%) of the desired aldehyde which can be reacted without any further purification.

The compounds listed in the table can be prepared by the same or similar methods.

The abbreviations used hereinbelow denote:

| r.i. | refractive index | m.p. | melting point |
|------|------------------|------|---------------|
| Et   | Ethyl            | Me   | Methyl        |
| Pr   | n-Propyl         | i-Pr | isopropyl     |
| c-Pr | cyclopropyl      | Bu   | n-Butyl       |
| Bn   | Benzyl           | Ph   | Phenyl        |

TABLE

Compounds of the formula (I) according to the invention

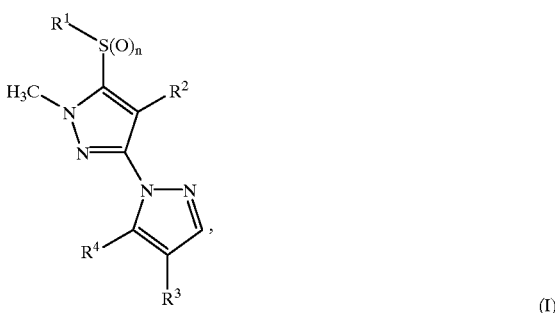

(I)

| No. | R¹ | n | R² | R³ | R⁴ | m.p. [° C.] or r.i. |
|---|---|---|---|---|---|---|
| 5 | Me | 2 | Cl | CN | CH(OPr)$_2$ | |
| 6 | Et | 2 | Cl | NO$_2$ | CO$_2$Pr | |
| 7 | Pr | 2 | Cl | CN | (CH$_2$)$_2$CO$_2$Et | |
| 8 | Me | 2 | Br | CN | CH(OMe)$_2$ | |
| 9 | Me | 2 | Cl | CN | CH$_2$CN | |
| 12 | Et | 2 | Cl | NO$_2$ | (CH$_2$)$_2$CN | |
| 11 | Me | 0 | Br | CN | CH(OEt)$_2$ | 106–107 |
| 12 | Me | 2 | Cl | CN | ![4-methyl-2-methyl-1,3-dioxane] | 155–158 |
| 13 | Et | 2 | Cl | CN | CH=CHCO$_2$Et | |
| 14 | Me | 2 | Br | CN | ![4-methyl-2-methyl-1,3-dioxane] | 166–168 |
| 15 | Me | 2 | Cl | CN | ![2-methyl-4-methyl-1,3-dioxane] | 153–157 |
| 16 | Me | 2 | Cl | CN | CH=CHCO$_2$CH$_2$C≡CH | |
| 17 | Et | 1 | Cl | NO$_2$ | (CH$_2$)$_2$C(OEt)$_3$ | |
| 18 | Me | 1 | Br | CN | CH(OEt)$_2$ | |
| 19 | Me | 2 | Cl | CN | CH$_2$C(OMe)$_3$ | |
| 20 | Et | 0 | Cl | NO$_2$ | CH=CHCO$_2$CH$_2$CH=CH$_2$ | |
| 21 | Pr | 1 | Br | CN | CCl=CClCO$_2$Pr | |
| 22 | Me | 2 | Cl | CN | CH=CHCO$_2$(CH$_2$)$_2$OMe | |
| 23 | Et | 2 | Br | NO$_2$ | CH=CClCO$_2$Et | |
| 24 | Me | 2 | Br | CN | ![2-methyl-4-methyl-1,3-dioxane] | 166–167 |
| 25 | Me | 2 | Br | CN | CH(OEt)$_2$ | |
| 26 | Me | 2 | Cl | CN | CH=CHCO$_2$CH$_2$CF$_3$ | |
| 27 | Et | 2 | Cl | CN | (CH$_2$)$_2$C(OEt)$_3$ | |

TABLE-continued

Compounds of the formula (I) according to the invention

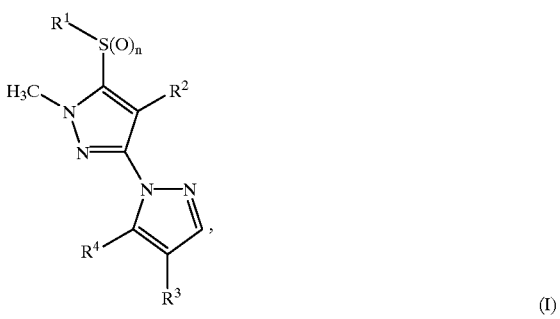

(I)

| No. | R¹ | n | R² | R³ | R⁴ | m.p. [° C.] or r.i. |
|---|---|---|---|---|---|---|
| 28 | Me | 2 | Cl | CN | ![2,4-dimethyl-1,3-dioxane] | 138–141 |
| 29 | Me | 2 | Br | CN | CH=CHCO₂CH₂CO₂Me | |
| 30 | Et | 2 | Cl | CN | C(=NH)OMe | |
| 31 | Me | 2 | Br | CN | CH₂CHClCN | |
| 32 | Me | 0 | Cl | CN | ![2-methyl-1,3-dioxane] | 115–118 |
| 33 | i-Pr | 0 | Cl | CN | ![methyl glycidate] | |
| 34 | Me | 2 | Br | CN | CH(OPr)₂ | |
| 35 | Me | 2 | Cl | C(=S)NH₂ | NMe₂ | |
| 36 | Et | 2 | Cl | CN | ![methyl 2-methylglycidate] | |
| 37 | Me | 2 | Cl | CN | NMe₂ | 151–153 |
| 38 | Et | 2 | Cl | NO₂ | ![1,3-dioxan-2-ylmethyl] | |
| 39 | Me | 2 | Cl | CN | ![2,5,5-trimethyl-1,3-dioxane] | 175–178 |
| 40 | Me | 2 | Cl | CN | ![1,3-dioxan-2-ylmethylamino] | 157–158 |
| 41 | Me | 2 | Br | CN | CH=CHCN | |
| 42 | Me | 2 | Br | CN | COCH₂C≡CH | |

TABLE-continued
Compounds of the formula (I) according to the invention
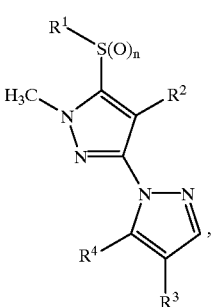
| No. | R¹ | n | R² | R³ | R⁴ | m.p. [° C.] or r.i. |
|---|---|---|---|---|---|---|
| 43 | c-Pr | 2 | Cl | CN | 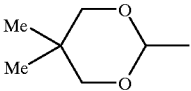 | |
| 44 | Me | 2 | Cl | C(=S)NH₂ | CO(CH₂)₂CO₂Et | |
| 45 | Me | 2 | Br | CN | 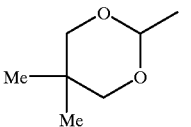 | 172–173 |
| 46 | Me | 2 | Cl | CN | C(=O)NEtMe | |
| 47 | Et | 2 | Cl | CN | 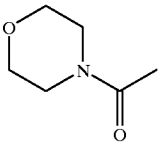 | |
| 48 | Pr | 0 | Br | NO₂ | CO(CH₂)₂CN | |
| 49 | Et | 2 | Cl | CN | CO₂(CH₂)₂OEt | |
| 50 | Me | 2 | Cl | CN | 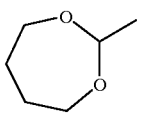 | 193–196 |
| 51 | Pr | 1 | Cl | NO₂ | CO₂CH₂CF₃ | |
| 52 | Me | 2 | Br | CN | CH=CHCO₂Et | |
| 53 | Me | 2 | Br | CN | COCF₃ | |
| 54 | Me | 2 | Br | CN | 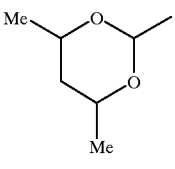 | 123–124 |
| 55 | Me | 2 | Cl | CN | COCH₂CF₃ | |
| 56 | Me | 1 | CN | CN | 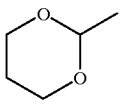 | 205–207 |
| 57 | Et | 2 | Cl | CN | CH₂OMe | 119–121 |
| 58 | Et | 2 | Cl | NO₂ | CH(NHMe)CHMeCN | |

TABLE-continued

Compounds of the formula (I) according to the invention

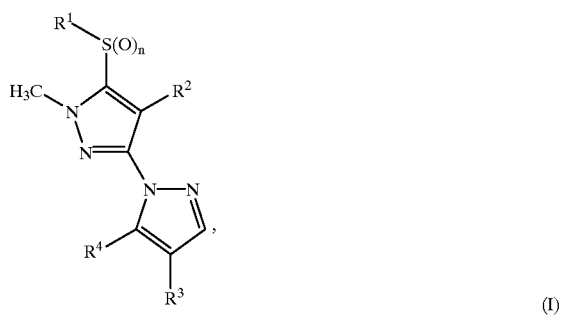

(I)

| No. | $R^1$ | n | $R^2$ | $R^3$ | $R^4$ | m.p. [° C.] or r.i. |
|---|---|---|---|---|---|---|
| 59 | Me | 2 | Br | CN | CHClCHMeCN | |
| 60 | Me | 2 | CN | CN | ![2,5,5-trimethyl-1,3-dioxane] | 202–205 |
| 61 | Et | 2 | Cl | $NO_2$ | CCl=CHCN | |
| 62 | i-Pr | 2 | Cl | CN | $CH(O(CH_2)_2OMe)_2$ | |
| 63 | Me | 2 | Br | CN | ![2-methyl-1,3-oxathiane] | |
| 64 | Et | 2 | Cl | $NO_2$ | $CH(OCH_2OMe)_2$ | |
| 65 | Me | 2 | Br | CN | $CH_2CHClCO_2Me$ | |
| 66 | Me | 2 | CN | CN | ![2-methyl-1,3-dioxepane] | 193–197 |
| 67 | Pr | 2 | Cl | $NO_2$ | $N(Me)CH_2CH=CH_2$ | |
| 68 | c-Pr | 2 | Cl | CN | NHCO-c-Pr | |
| 69 | Me | 2 | Br | CN | NHCO-i-Pr | |
| 70 | Me | 2 | Cl | $NO_2$ | $CH_2CHClCO_2Me$ | |
| 71 | Me | 2 | Br | CN | ![2-methyl-1,3-dioxepane] | |
| 72 | Me | 2 | Cl | CN | $NHCH_2CH(OMe)_2$ | 156–158 |
| 73 | Me | 2 | Cl | $NO_2$ | CH=CHCN | |
| 74 | Me | 2 | Br | CN | $CH=CHCO_2Me$ | |
| 75 | Me | 2 | Cl | CN | ![2-methyl-4,7-dihydro-1,3-dioxepine] | 193–198 |
| 76 | Et | 2 | CN | $NO_2$ | $CH_2O(CH_2)_2OMe$ | |
| 77 | Me | 2 | Cl | CN | $CH_2CHClCO_2Et$ | |
| 78 | Me | 2 | Cl | CN | $CH=CHCO_2Me$ | |
| 79 | Me | 2 | Cl | CN | NEtMe | 113–115 |

TABLE-continued

Compounds of the formula (I) according to the invention

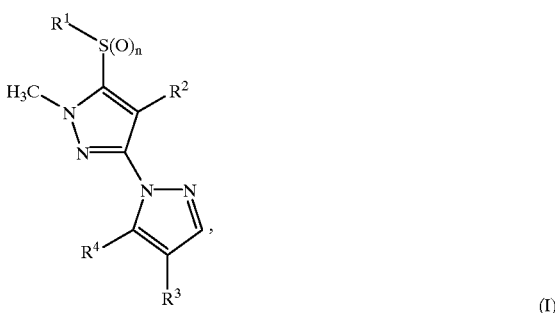

(I)

| No. | R¹ | n | R² | R³ | R⁴ | m.p. [° C.] or r.i. |
|---|---|---|---|---|---|---|
| 80 | Me | 2 | Cl | CN | (2-methyl-5-methylene-1,3-dioxane) | 160–163 |
| 81 | Et | 2 | Cl | NO₂ | CH₂O(CH₂)₂OMe | |
| 82 | Me | 2 | Cl | CN | CH₂CCl₃ | |
| 83 | Me | 2 | Br | CN | CH₂CHClCO₂Et | |
| 84 | Me | 2 | CN | CN | (2-methyl-1,3-dioxane) | 217–219 |
| 85 | Me | 2 | Br | CN | CH₂CCl₃ | |
| 86 | Me | 2 | Br | CN | (2-methyl-4,7-dihydro-1,3-dioxepine) | |
| 87 | Et | 2 | Cl | NO₂ | CH₂O(CH₂)₂OMe | |
| 88 | Me | 2 | Cl | CN | NHMe | 205–206 |
| 89 | Me | 2 | Cl | CN | (2,4,4-trimethyl-1,3-dioxane) | $n_D^{20} = 1.5209$ |
| 90 | Me | 2 | Cl | NO₂ | CH₂CHClCO₂Me | |
| 91 | Me | 2 | Cl | CN | NH-iPr | 200–202 |
| 92 | i-Pr | 2 | Br | CN | C(=NH)OEt | |
| 93 | Me | 2 | Cl | CN | CH₂CO₂Me | |
| 94 | Me | 2 | Cl | CN | Br | 160 |
| 95 | Me | 0 | CN | CN | (2-methyl-1,3-dioxane) | 156–158 |
| 96 | Me | 2 | Br | CN | (2-methyl-5-methylene-1,3-dioxane) | Resin |

TABLE-continued

Compounds of the formula (I) according to the invention

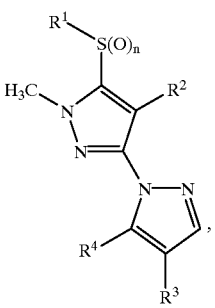

(I)

| No. | R¹ | n | R² | R³ | R⁴ | m.p. [° C.] or r.i. |
|---|---|---|---|---|---|---|
| 97 | Me | 2 | Cl | CN | 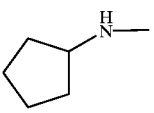 | 190–192 |
| 98 | Me | 2 | Cl | CN | 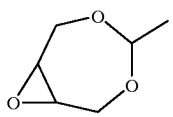 | |
| 99 | Me | 2 | CN | CN | 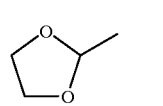 | 201–204 |
| 100 | Me | 2 | Cl | NO₂ | CH₂CHClCN | |
| 101 | Me | 2 | Cl | CN | CH₂Cl | |
| 102 | i-Pr | 2 | Br | NO₂ | CH₂S(CH₂)₂OMe | |
| 103 | Me | 2 | Cl | CN | CH₂CO₂Et | |
| 104 | Me | 2 | Iod | CN | 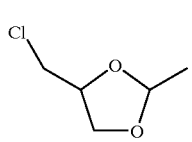 | Resin |
| 105 | Me | 0 | CN | CN | CH(OEt)₂ | 95–97 |
| 106 | i-Pr | 2 | Cl | NO₂ | CH₂O(CH₂)₂SMe | |
| 107 | Me | 2 | Cl | CN | CH₂CH(OMe)₂ | |
| 108 | Et | 2 | Br | NO₂ | CH₂O(CH₂)₃OEt | |
| 109 | Pr | 2 | Cl | CN | C≡CCO₂Pr | |
| 110 | Me | 1 | CN | CN | CH(OEt)₂ | 163–167 |
| 111 | Me | 2 | Br | CN | 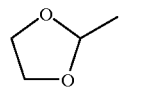 | 156–157 |
| 112 | i-Pr | 2 | Cl | NO₂ | CHMeCHCO₂Et | |
| 113 | Me | 2 | Cl | CN | NEt₂ | 127–128 |
| 114 | Et | 2 | Cl | CN | CHBrCHMeCN | |
| 115 | Me | 2 | CN | CN | CH(OEt)₂ | 135–137 |
| 116 | i-Pr | 2 | Cl | NO₂ | CH₂O(CH₂)₂OBu | |
| 117 | Me | 2 | Cl | CN | 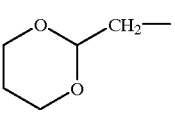 | |
| 118 | Et | 2 | Cl | CN | CBr=CHCN | |
| 119 | Me | 1 | Cl | CN | CH(OEt)₂ | 129–135 |
| 120 | Et | 2 | CN | NO₂ | C≡CCN | |

TABLE-continued

Compounds of the formula (I) according to the invention

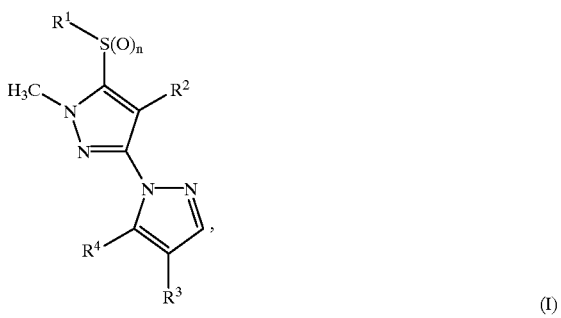

(I)

| No. | R¹ | n | R² | R³ | R⁴ | m.p. [° C.] or r.i. |
|---|---|---|---|---|---|---|
| 121 | Me | 2 | Br | CN | CH$_2$CO$_2$Et | |
| 122 | Me | 2 | Cl | CN | CH(OCH$_2$CH$_2$OMe)$_2$ | 87–89 |
| 123 | Me | 2 | Cl | CN | N(Me)CH$_2$CH=CH | 122–123 |
| 124 | Et | 2 | Br | CN | C≡CCOMe | |
| 125 | Me | 1 | Cl | CN | NEt$_2$ | 161–163 |
| 126 | Me | 2 | Cl | CN | (CH$_2$)$_2$C(=NH)OMe | |
| 127 | Me | 2 | Cl | NO$_2$ | CH$_2$CHClCO$_2$Et | |
| 128 | Me | 2 | Cl | NO$_2$ | CH=CHCO$_2$Et | |
| 129 | Me | 2 | Cl | CN | CH$_2$SMe | 144–145 |
| 130 | Me | 2 | Cl | CN | NHCOEt | 231–233 |
| 131 | Me | 2 | Cl | CN | NHCOMe | 226–228 |
| 132 | Me | 2 | Br | CN | CH$_2$CO$_2$Me | |
| 133 | Pr | 2 | Cl | CN | CO$_2$CF$_3$ | |
| 134 | Me | 2 | Cl | CN | CH$_2$O(CH$_2$)$_2$OMe | 86.5–88 |
| 135 | i-Pr | 1 | Cl | NO$_2$ | CO(CH$_2$)$_2$OEt | |
| 136 | Me | 2 | Cl | CN | CH$_2$OPr | 114–115 |
| 137 | Me | 2 | Cl | CN | C(=NH)OEt | |
| 138 | Me | 2 | Cl | CN | CONMeEt | |
| 139 | Me | 2 | Cl | CN | CH$_2$OMe | 89.5–91 |
| 140 | Me | 2 | Cl | CN | O(CH$_2$)$_2$OMe | |
| 141 | Me | 2 | Cl | CN | OEt | |
| 142 | Me | 1 | Cl | CN | CH$_2$OMe | 98–99 |
| 143 | Me | 2 | Cl | CN | SMe | |
| 144 | Me | 2 | Cl | CN | [1,3-dioxolan-2-ylmethylamino] | 148–150 |
| 145 | Me | 0 | Cl | CN | [4-methyl-2-methyl-1,3-dioxane] | Oil |
| 146 | Me | 0 | Cl | CN | [5,5-dimethyl-2-methyl-1,3-dioxane with Me] | Resin |
| 147 | Me | 0 | Cl | CN | [5,5-diethyl-2-methyl-1,3-dioxane] | Resin |
| 148 | Me | 0 | Cl | CN | [5-ethyl-5-methyl-2-methyl-1,3-dioxane] | Resin |

TABLE-continued

Compounds of the formula (I) according to the invention (I)

| No. | R¹ | n | R² | R³ | R⁴ | m.p. [° C.] or r.i. |
|-----|-----|---|-----|-----|-----|---------------------|
| 149 | Me | 0 | Cl | CN | 5,5-bis(bromomethyl)-2-methyl-1,3-dioxane | Resin |
| 150 | Me | 0 | Cl | CN | 5-ethyl-2-methyl-5-propyl-1,3-dioxane | Resin |
| 151 | Me | 0 | Cl | CN | 2,5-dimethyl-1,3-dioxane | Resin |
| 152 | Me | 0 | Cl | CN | 2,4,6,6-tetramethyl-1,3-dioxane | Resin |
| 153 | Me | 0 | Cl | CN | 5-ethyl-2-methyl-5-propyl-1,3-dioxane | Resin |
| 154 | Me | 0 | Cl | CN | 4-isopropyl-2,5,5-trimethyl-1,3-dioxane | Resin |
| 155 | Me | 0 | Cl | CN | 5-butyl-5-ethyl-2-methyl-1,3-dioxane | Resin |
| 156 | Me | 0 | Cl | CN | 5-methoxy-2-methyl-1,3-dioxane | Resin |

US 6,232,271 B1
TABLE-continued
Compounds of the formula (I) according to the invention
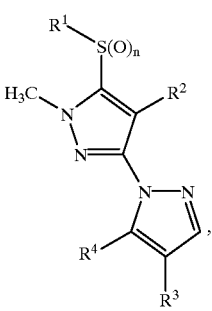
(I)
| No. | R¹ | n | R² | R³ | R⁴ | m.p. [° C.] or r.i. |
|---|---|---|---|---|---|---|
| 157 | Me | 0 | Cl | CN | 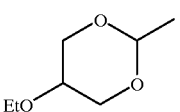 | Resin |
| 158 | Me | 0 | Cl | CN | 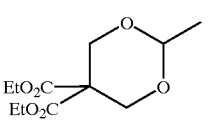 | Resin |
| 159 | Me | 0 | Cl | CN | 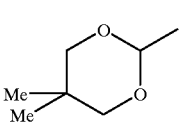 | Resin |
| 160 | Me | 0 | Cl | CN | 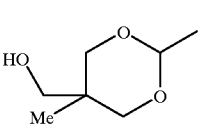 | Resin |
| 161 | Me | 0 | Cl | CN | 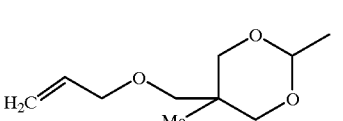 | Resin |
| 162 | Me | 0 | Cl | CN | 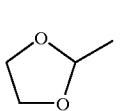 | Resin |
| 163 | Me | 0 | Cl | CN | 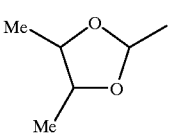 | Resin |
| 164 | Me | 0 | Cl | CN | 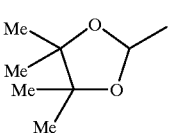 | Resin |
| 165 | Me | 0 | Cl | CN | 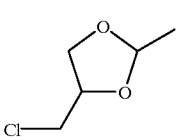 | Resin |

TABLE-continued
Compounds of the formula (I) according to the invention
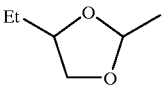
(I)
| No. | R¹ | n | R² | R³ | R⁴ | m.p. [° C.] or r.i. |
|---|---|---|---|---|---|---|
| 166 | Me | 0 | Cl | CN | 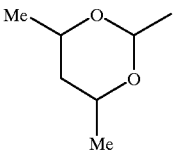 | Resin |
| 167 | Me | 0 | Cl | CN | 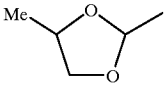 | Resin |
| 168 | Me | 0 | Cl | CN | 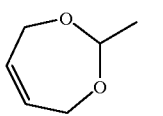 | Resin |
| 169 | Me | 0 | Cl | CN | 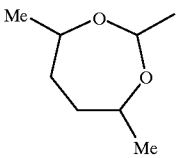 | semi-crystal |
| 170 | Me | 0 | Cl | CN | 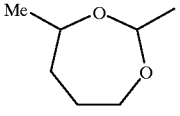 | semi-crystal |
| 171 | Me | 0 | Cl | CN | 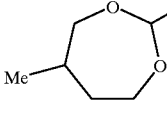 | semi-crystal |
| 172 | Me | 0 | Cl | CN | 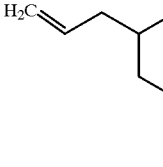 | semi-crystal |
| 173 | Me | 0 | Cl | CN |  | Resin |

TABLE-continued
Compounds of the formula (I) according to the invention
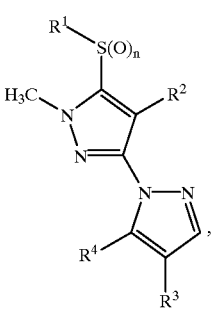
(I)
| No. | R¹ | n | R² | R³ | R⁴ | m.p. [° C.] or r.i. |
|---|---|---|---|---|---|---|
| 174 | Me | 0 | Cl | CN | 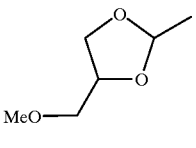 | Resin |
| 175 | Me | 0 | Cl | CN | 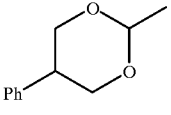 | Resin |
| 176 | Me | 0 | Cl | CN | 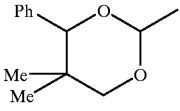 | Resin |
| 177 | Me | 0 | Cl | CN | 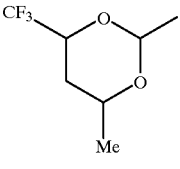 | Resin |
| 178 | Me | 0 | Cl | CN | 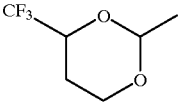 | Resin |
| 179 | Me | 0 | Cl | CN | 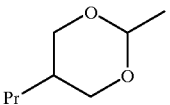 | Resin |
| 180 | Me | 0 | Cl | CN | 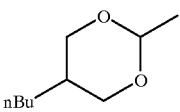 | Resin |
| 181 | Me | 0 | Cl | CN |  | Resin |

TABLE-continued
Compounds of the formula (I) according to the invention
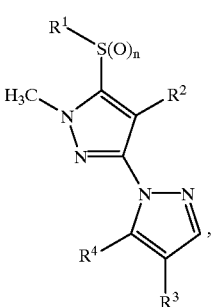
(I)
| No. | R¹ | n | R² | R³ | R⁴ | m.p. [° C.] or r.i. |
|---|---|---|---|---|---|---|
| 182 | Me | 0 | Cl | CN | 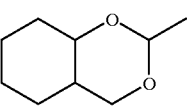 | Resin |
| 183 | Me | 0 | Cl | CN | 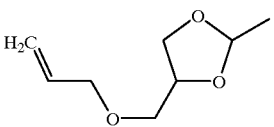 | Resin |
| 184 | Me | 0 | Cl | CN | 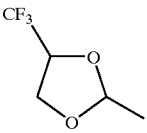 | Resin |
| 185 | Me | 0 | Cl | CN | 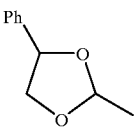 | Resin |
| 186 | Me | 0 | Cl | CN | 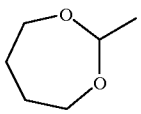 | Resin |
| 187 | Me | 0 | Cl | CN | 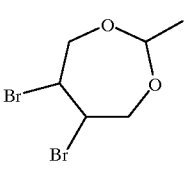 | Resin |
| 188 | Me | 0 | Cl | CN | 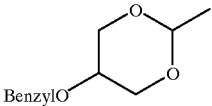 | Resin |
| 189 | Me | 0 | Cl | CN | 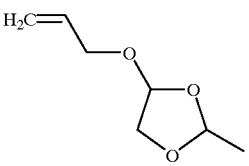 | Resin |

TABLE-continued

Compounds of the formula (I) according to the invention

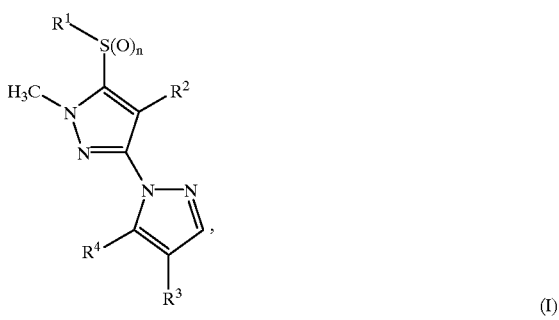

(I)

| No. | R¹ | n | R² | R³ | R⁴ | m.p. [° C.] or r.i. |
|---|---|---|---|---|---|---|
| 190 | Me | 0 | Cl | CN | Me-O, Me-O-substituted 2-methyl-1,3-dioxolane | Resin |
| 191 | Me | 0 | Cl | CN | BenzylO-CH₂-(2-methyl-1,3-dioxolan-4-yl) | Resin |
| 192 | Me | 0 | Cl | CN | Me₂N-CH₂-(2-methyl-1,3-dioxolan-4-yl) | Resin |
| 193 | Me | 0 | Cl | CN | PhOCH₂-(2-methyl-1,3-dioxolan-4-yl) | Resin |
| 194 | Me | 0 | Cl | CN | MeS-CH₂-(2-methyl-1,3-dioxolan-4-yl) | Resin |
| 195 | Me | 0 | Cl | CN | CH₂=,CH₂=-disubstituted 2-methyl-1,3-dioxolane | Resin |
| 196 | Me | 0 | Cl | CN | EtO-CH₂-(2-methyl-1,3-dioxolan-4-yl) | Resin |
| 197 | Me | 0 | Cl | CN | EtS-CH₂-(2-methyl-1,3-dioxolan-4-yl) | Resin |

TABLE-continued
Compounds of the formula (I) according to the invention
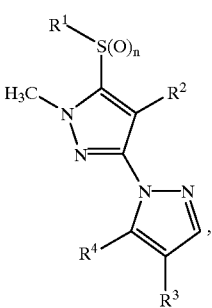
(I)
| No. | R¹ | n | R² | R³ | R⁴ | m.p. [° C.] or r.i. |
|---|---|---|---|---|---|---|
| 198 | Me | 0 | Cl | CN | 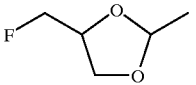 | Resin |
| 199 | Me | 0 | Cl | CN | 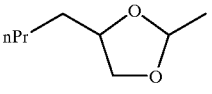 | Resin |
| 200 | Me | 0 | Cl | CN | 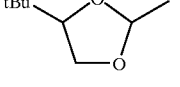 | Resin |
| 201 | Me | 0 | Cl | CN | 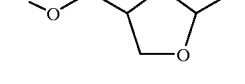 | Resin |
| 202 | Me | 0 | Cl | CN | 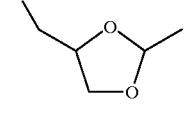 | Resin |
| 203 | Me | 0 | Cl | CN | 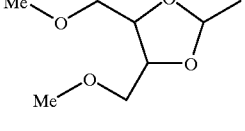 | Resin |
| 204 | Me | 0 | Cl | CN | 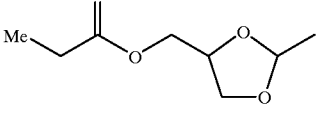 | Resin |
| 205 | Me | 0 | Cl | CN | 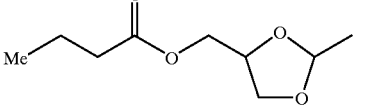 | Resin |
| 206 | Me | 0 | Cl | CN | 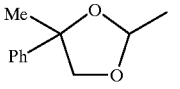 | Resin |

TABLE-continued
Compounds of the formula (I) according to the invention
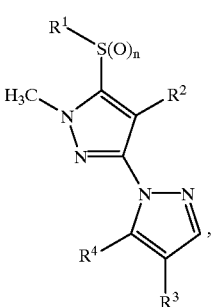
(I)
| No. | R¹ | n | R² | R³ | R⁴ | m.p. [° C.] or r.i. |
|---|---|---|---|---|---|---|
| 207 | Me | 0 | Cl | CN | 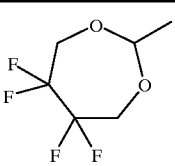 | Resin |
| 208 | Me | 0 | Cl | CN | 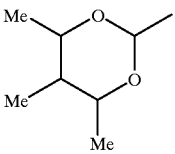 | Resin |
| 209 | Me | 0 | Br | CN | 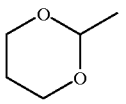 | Resin |
| 210 | Me | 0 | Br | CN | 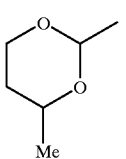 | Viskoses oil |
| 211 | Me | 0 | Br | CN | 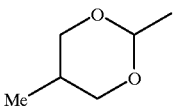 | Resin |
| 212 | Me | 0 | Br | CN | 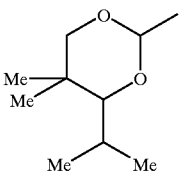 | Resin |
| 213 | Me | 0 | Br | CN | 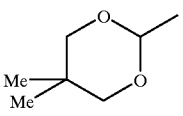 | Resin |
| 214 | Me | 0 | Br | CN | 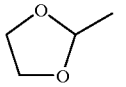 | Resin |

TABLE-continued

Compounds of the formula (I) according to the invention

| No. | R¹ | n | R² | R³ | R⁴ | m.p. [° C.] or r.i. |
|-----|----|----|----|----|----|----|
| 215 | Me | 0 | Br | CN | 4,5-dimethyl-2-methyl-1,3-dioxolane | Viscous oil |
| 216 | Me | 0 | Br | CN | 4,6-dimethyl-2-methyl-1,3-dioxane | Resin |
| 217 | Me | 0 | Br | CN | 4-methyl-2-methyl-1,3-dioxolane | Resin |
| 218 | Me | 0 | Br | CN | 2-methyl-4,7-dihydro-1,3-dioxepine | Resin |
| 219 | Me | 0 | Br | CN | 4,7-dimethyl-2-methyl-1,3-dioxepane | Resin |
| 220 | Me | 0 | Br | CN | 4-methyl-1,3-dioxepane | Resin |
| 221 | Me | 0 | Br | CN | 2-methyl-1,3-dioxepane | Resin |
| 222 | Me | 0 | Br | CN | 4-phenyl-5,5-dimethyl-2-methyl-1,3-dioxane | Resin |

TABLE-continued
Compounds of the formula (I) according to the invention
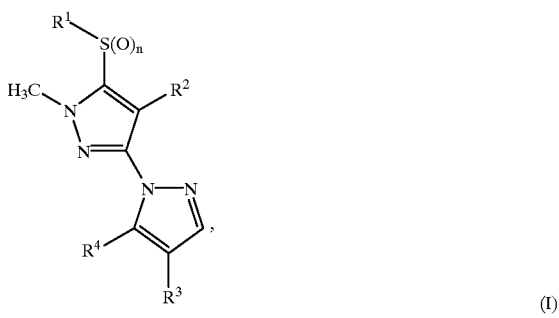
(I)
| No. | R¹ | n | R² | R³ | R⁴ | m.p. [° C.] or r.i. |
|-----|----|----|----|----|----|---------------------|
| 223 | Me | 0 | Br | CN | 4-CF₃-6-Me-1,3-dioxan-2-yl | Resin |
| 224 | Me | 0 | Br | CN | 4-CF₃-1,3-dioxan-2-yl | Resin |
| 225 | Me | 0 | Br | CN | 5-nBu-1,3-dioxan-2-yl | Resin |
| 226 | Me | 0 | Br | CN | 4-CF₃-1,3-dioxolan-2-yl | Resin |
| 227 | Me | 0 | Br | CN | 4-Ph-1,3-dioxolan-2-yl | Resin |
| 228 | Me | 0 | Br | CN | 5,6-diBr-1,3-dioxepan-2-yl | Resin |
| 229 | Me | 0 | Br | CN | 4-(allyloxy)-1,3-dioxolan-2-yl | Resin |

TABLE-continued
Compounds of the formula (I) according to the invention
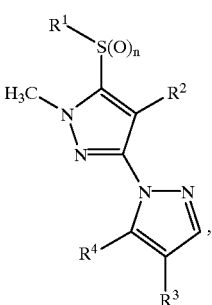
(I)
| No. | R¹ | n | R² | R³ | R⁴ | m.p. [° C.] or r.i. |
|---|---|---|---|---|---|---|
| 230 | Me | 0 | Br | CN | 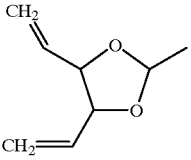 | Resin |
| 231 | Me | 0 | Br | CN | 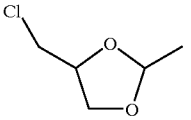 | Resin |
| 232 | Me | 0 | Br | CN | 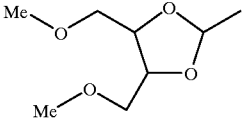 | Resin |
| 233 | Me | 1 | Cl | CN | 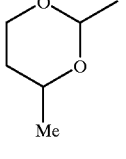 | Resin |
| 234 | Me | 1 | Cl | CN | 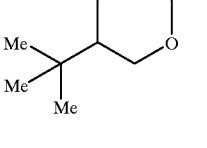 | Resin |
| 235 | Me | 1 | Cl | CN | 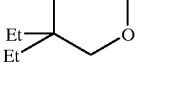 | Resin |
| 236 | Me | 1 | Cl | CN | 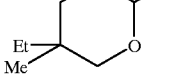 | Resin |
| 237 | Me | 1 | Cl | CN | 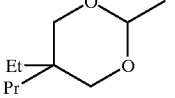 | Resin |

TABLE-continued

Compounds of the formula (I) according to the invention

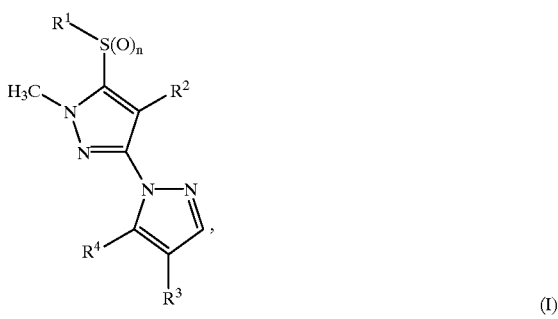

(I)

| No. | R¹ | n | R² | R³ | R⁴ | m.p. [° C.] or r.i. |
|---|---|---|---|---|---|---|
| 238 | Me | 1 | Cl | CN | 5-methyl-1,3-dioxan-2-yl | Resin |
| 239 | Me | 1 | Cl | CN | 4,4,6-trimethyl-1,3-dioxan-2-yl | Resin |
| 240 | Me | 1 | Cl | CN | 5,5-dimethyl-4-(isopropyl)-1,3-dioxan-2-yl derivative | Resin |
| 241 | Me | 1 | Cl | CN | 5-butyl-5-ethyl-1,3-dioxan-2-yl | Resin |
| 242 | Me | 1 | Cl | CN | 5-methoxy-1,3-dioxan-2-yl | Resin |
| 243 | Me | 1 | Cl | CN | 5-ethoxy-1,3-dioxan-2-yl | Resin |
| 244 | Me | 1 | Cl | CN | 5,5-dimethyl-1,3-dioxan-2-yl | Resin |
| 245 | Me | 1 | Cl | CN | 5-(hydroxymethyl)-5-methyl-1,3-dioxan-2-yl | Resin |

TABLE-continued

Compounds of the formula (I) according to the invention

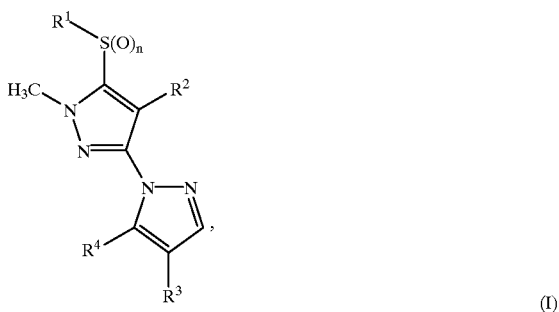

(I)

| No. | R¹ | n | R² | R³ | R⁴ | m.p. [° C.] or r.i. |
|---|---|---|---|---|---|---|
| 246 | Me | 1 | Cl | CN | 1,3-dioxolan-2-yl | Resin |
| 247 | Me | 1 | Cl | CN | 4,5-dimethyl-1,3-dioxolan-2-yl | Resin |
| 248 | Me | 1 | Cl | CN | 4,4,5,5-tetramethyl-1,3-dioxolan-2-yl | Resin |
| 249 | Me | 1 | Cl | CN | 4-(chloromethyl)-1,3-dioxolan-2-yl | Resin |
| 250 | Me | 1 | Cl | CN | 4-ethyl-1,3-dioxolan-2-yl | Resin |
| 251 | Me | 1 | Cl | CN | 4,6-dimethyl-1,3-dioxan-2-yl | Resin |
| 252 | Me | 1 | Cl | CN | 4-methyl-1,3-dioxolan-2-yl | Resin |
| 253 | Me | 1 | Cl | CN | 2-methyl-4,7-dihydro-1,3-dioxepin-2-yl | semi-crystal |

TABLE-continued

Compounds of the formula (I) according to the invention

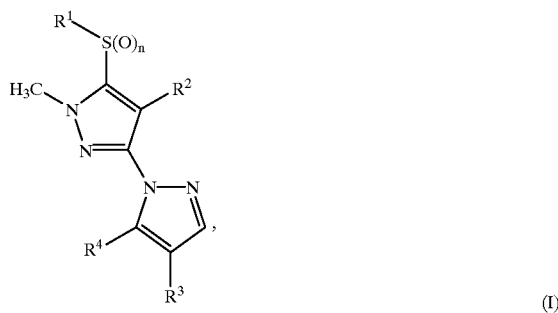

(I)

| No. | R¹ | n | R² | R³ | R⁴ | m.p. [° C.] or r.i. |
|---|---|---|---|---|---|---|
| 254 | Me | 1 | Cl | CN | Me−⟨7-membered 1,3-dioxepane with 2-Me and other-Me⟩ | Resin |
| 255 | Me | 1 | Cl | CN | Me−⟨7-membered 1,3-dioxepane with 2-Me⟩ | Resin |
| 256 | Me | 1 | Cl | CN | Me−⟨7-membered 1,3-dioxepane with 2-Me⟩ | Resin |
| 257 | Me | 1 | Cl | CN | H₂C=CH−CH₂−⟨1,3-dioxane with 2-Me, 6-Me⟩ | Resin |
| 258 | Me | 1 | Cl | CN | MeO−CH₂−⟨1,3-dioxolane with 2-Me⟩ | Resin |
| 259 | Me | 1 | Cl | CN | Bu−⟨1,3-dioxane with 2-Me⟩ | Resin |
| 260 | Me | 1 | Cl | CN | Ph−⟨1,3-dioxane with 2-Me⟩ | Resin |
| 261 | Me | 1 | Cl | CN | Ph, Me, Me−⟨1,3-dioxane with 2-Me⟩ | Resin |

TABLE-continued

Compounds of the formula (I) according to the invention

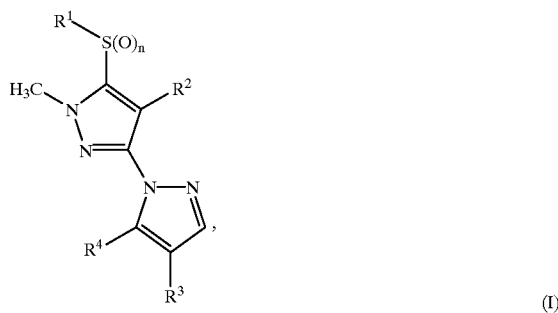

(I)

| No. | R$^1$ | n | R$^2$ | R$^3$ | R$^4$ | m.p. [° C.] or r.i. |
|---|---|---|---|---|---|---|
| 262 | Me | 1 | Cl | CN | 4-CF$_3$-2-methyl-1,3-dioxane | Resin |
| 263 | Me | 1 | Cl | CN | 5-nPr-2-methyl-1,3-dioxane | Resin |
| 264 | Me | 1 | Cl | CN | 2-methyl-hexahydro-4H-1,3-benzodioxine | Resin |
| 265 | Me | 1 | Cl | CN | 4-(allyloxymethyl)-2-methyl-1,3-dioxolane | Resin |
| 266 | Me | 1 | Cl | CN | 4-Ph-2-methyl-1,3-dioxolane | Resin |
| 267 | Me | 1 | Cl | CN | 2-methyl-1,3-dioxepane | Resin |
| 268 | Me | 1 | Cl | CN | 5,6-dibromo-2-methyl-1,3-dioxepane | Resin |
| 269 | Me | 1 | Br | CN | 4-Me-2-methyl-1,3-dioxane | Resin |

TABLE-continued
Compounds of the formula (I) according to the invention
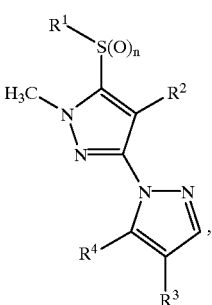
(I)
| No. | R¹ | n | R² | R³ | R⁴ | m.p. [° C.] or r.i. |
|---|---|---|---|---|---|---|
| 270 | Me | 1 | Br | CN | 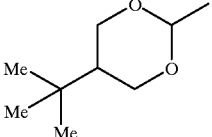 | Resin |
| 271 | Me | 1 | Br | CN | 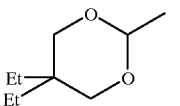 | Resin |
| 272 | Me | 1 | Br | CN | 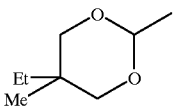 | Resin |
| 273 | Me | 1 | Br | CN | 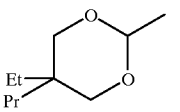 | Resin |
| 274 | Me | 1 | Br | CN | 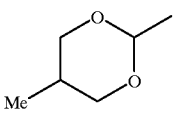 | Resin |
| 275 | Me | 1 | Br | CN | 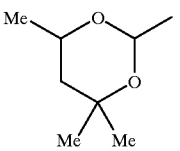 | Resin |
| 276 | Me | 1 | Br | CN | 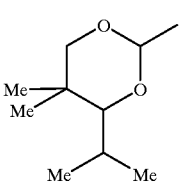 | Resin |
| 277 | Me | 1 | Br | CN | 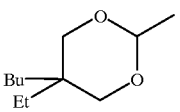 | Resin |

TABLE-continued
Compounds of the formula (I) according to the invention
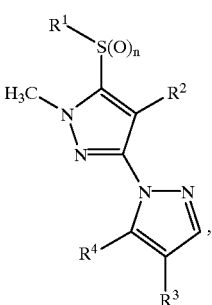
| No. | R¹ | n | R² | R³ | R⁴ | m.p. [° C.] or r.i. |
|---|---|---|---|---|---|---|
| 278 | Me | 1 | Br | CN | 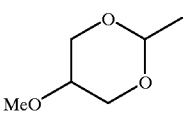 | Resin |
| 279 | Me | 1 | Br | CN | 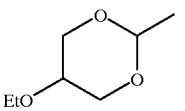 | Resin |
| 280 | Me | 1 | Br | CN | 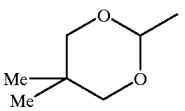 | Resin |
| 281 | Me | 1 | Br | CN | 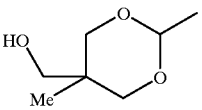 | Resin |
| 282 | Me | 1 | Br | CN | 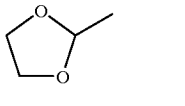 | Resin |
| 283 | Me | 1 | Br | CN | 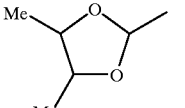 | Resin |
| 284 | Me | 1 | Br | CN | 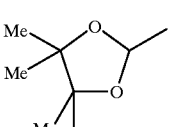 | Resin |
| 285 | Me | 1 | Br | CN | 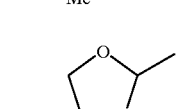 | Resin |
| 286 | Me | 1 | Br | CN | 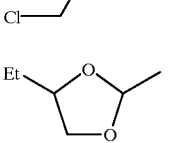 | Resin |

TABLE-continued
Compounds of the formula (I) according to the invention
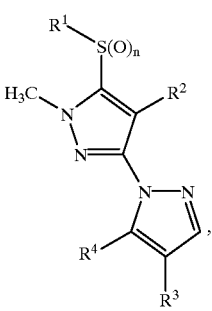
(I)
| No. | R¹ | n | R² | R³ | R⁴ | m.p. [° C.] or r.i. |
|-----|----|----|----|----|----|---------------------|
| 287 | Me | 1 | Br | CN | 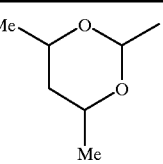 | Resin |
| 288 | Me | 1 | Br | CN | 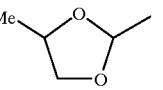 | Resin |
| 289 | Me | 1 | Br | CN | 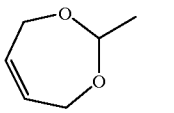 | semi-crystal |
| 290 | Me | 1 | Br | CN | 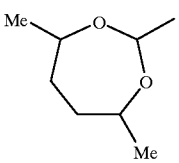 | Resin |
| 291 | Me | 1 | Br | CN | 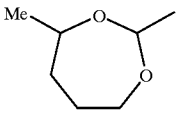 | Resin |
| 292 | Me | 1 | Br | CN | 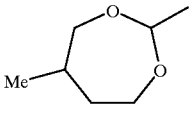 | Resin |
| 293 | Me | 1 | Br | CN | 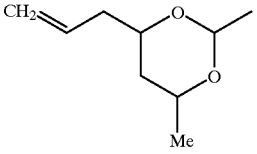 | Resin |
| 294 | Me | 1 | Br | CN | 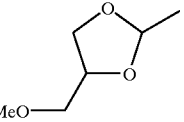 | Resin |

TABLE-continued

Compounds of the formula (I) according to the invention

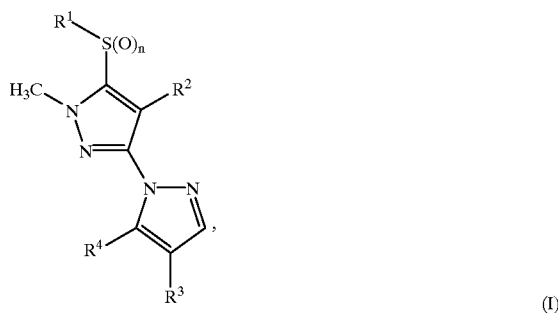

(I)

| No. | R¹ | n | R² | R³ | R⁴ | m.p. [° C.] or r.i. |
|-----|----|----|----|----|----|-----|
| 295 | Me | 1 | Br | CN | 2-methyl-5-butyl-1,3-dioxane | Resin |
| 296 | Me | 1 | Br | CN | 2-methyl-5-phenyl-1,3-dioxane | Resin |
| 297 | Me | 1 | Br | CN | 2-methyl-5,5-dimethyl-4-phenyl-1,3-dioxane | Resin |
| 298 | Me | 1 | Br | CN | 2-methyl-5-nPr-1,3-dioxane | Resin |
| 299 | Me | 1 | Br | CN | 2-methyl-4-(allyloxymethyl)-1,3-dioxolane | Resin |
| 300 | Me | 1 | Br | CN | 2-methyl-4-phenyl-1,3-dioxolane | Resin |
| 301 | Me | 1 | Br | CN | 2-methyl-1,3-dioxepane | Resin |
| 302 | Me | 1 | Br | CN | 2-methyl-5,6-dibromo-1,3-dioxepane | Resin |

TABLE-continued
Compounds of the formula (I) according to the invention
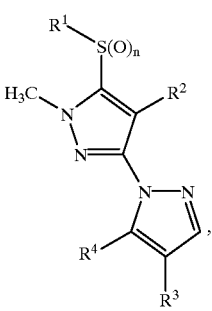
(I)
| No. | R¹ | n | R² | R³ | R⁴ | m.p. [° C.] or r.i. |
|-----|----|---|----|----|-----|---------------------|
| 303 | Me | 2 | Cl | CN | 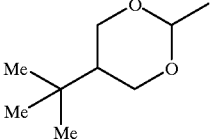 | Resin |
| 304 | Me | 2 | Cl | CN | 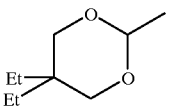 | 130–131 |
| 305 | Me | 2 | Cl | CN | 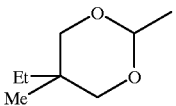 | 134–135 |
| 306 | Me | 2 | Cl | CN | 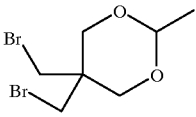 | Resin |
| 307 | Me | 2 | Cl | CN | 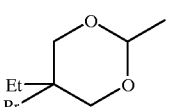 | Resin |
| 308 | Me | 2 | Cl | CN | 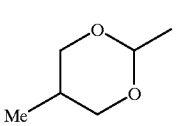 | Resin |
| 309 | Me | 2 | Cl | CN | 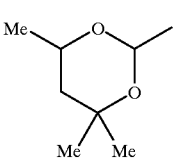 | Resin |
| 310 | Me | 2 | Cl | CN | 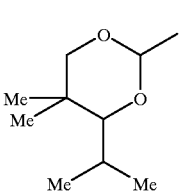 | Resin |

TABLE-continued

Compounds of the formula (I) according to the invention

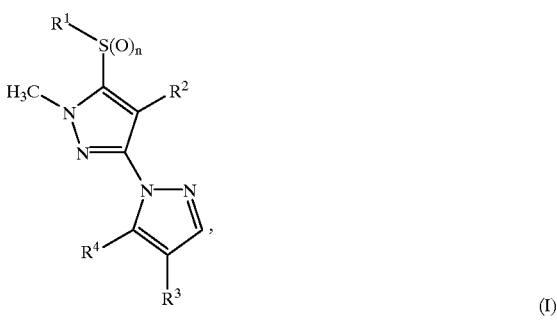

(I)

| No. | R¹ | n | R² | R³ | R⁴ | m.p. [° C.] or r.i. |
|-----|----|----|----|----|----|----|
| 311 | Me | 2 | Cl | CN | 2-methyl-5-nBu-5-Et-1,3-dioxane | Resin |
| 312 | Me | 2 | Cl | CN | 2-methyl-5-MeO-1,3-dioxane | Resin |
| 313 | Me | 2 | Cl | CN | 2-methyl-5-EtO-1,3-dioxane | Resin |
| 304 | Me | 2 | Cl | CN | 2-methyl-5,5-bis(EtO₂C)-1,3-dioxane | Resin |
| 315 | Me | 2 | Cl | CN | 2-methyl-5-(HOCH₂)-5-Me-1,3-dioxane | Resin |
| 316 | Me | 2 | Cl | CN | 2-methyl-5-(H₂C=CHCH₂OCH₂)-5-Me-1,3-dioxane | Resin |
| 317 | Me | 2 | Cl | CN | 2,4,5-trimethyl-1,3-dioxolane | 135–137 |
| 318 | Me | 2 | Cl | CN | 2,4,4,5,5-pentamethyl-1,3-dioxolane | Resin |

TABLE-continued
Compounds of the formula (I) according to the invention
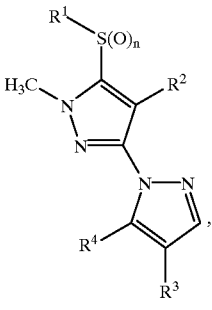
(I)
| No. | R¹ | n | R² | R³ | R⁴ | m.p. [° C.] or r.i. |
|---|---|---|---|---|---|---|
| 319 | Me | 2 | Cl | CN | 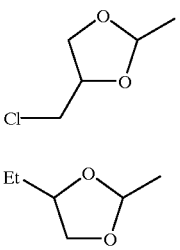 | 105–107 |
| 320 | Me | 2 | Cl | CN | 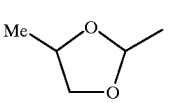 | 118–122 |
| 321 | Me | 2 | Cl | CN | 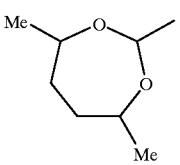 | 128–129 |
| 322 | Me | 2 | Cl | CN | 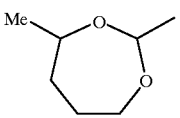 | Resin |
| 323 | Me | 2 | Cl | CN | 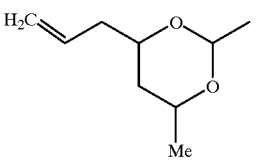 | Resin |
| 324 | Me | 2 | Cl | CN | 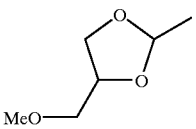 | Resin |
| 325 | Me | 2 | Cl | CN | 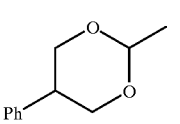 | Resin |
| 326 | Me | 2 | Cl | CN |  | Resin |

TABLE-continued

Compounds of the formula (I) according to the invention

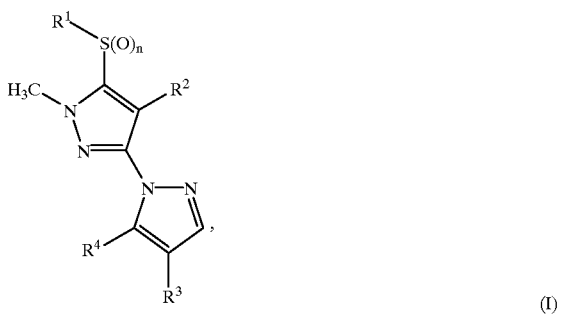

(I)

| No. | R¹ | n | R² | R³ | R⁴ | m.p. [° C.] or r.i. |
|---|---|---|---|---|---|---|
| 327 | Me | 2 | Cl | CN | 4-Ph-5,5-diMe-2-Me-1,3-dioxan-4-yl | Resin |
| 328 | Me | 2 | Cl | CN | 4-CF₃-6-Me-2-Me-1,3-dioxan-4-yl | Resin |
| 329 | Me | 2 | Cl | CN | 4-CF₃-2-Me-1,3-dioxan-4-yl | Resin |
| 330 | Me | 2 | Cl | CN | 5-Pr-2-Me-1,3-dioxan-2-yl | Resin |
| 331 | Me | 2 | Cl | CN | 5-Bu-2-Me-1,3-dioxan-2-yl | Resin |
| 332 | Me | 2 | Cl | CN | 2-Me-hexahydro-1,3-benzodioxin-2-yl | Resin |
| 333 | Me | 2 | Cl | CN | 4-(allyloxymethyl)-2-Me-1,3-dioxolan-2-yl | Resin |
| 334 | Me | 2 | Cl | CN | 4-CF₃-2-Me-1,3-dioxolan-2-yl | Resin |

TABLE-continued
Compounds of the formula (I) according to the invention
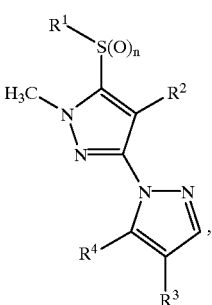
(I)
| No. | R¹ | n | R² | R³ | R⁴ | m.p. [° C.] or r.i. |
|---|---|---|---|---|---|---|
| 335 | Me | 2 | Cl | CN | 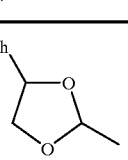 | Resin |
| 336 | Me | 2 | Cl | CN | 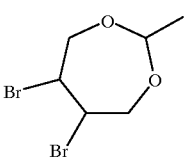 | Resin |
| 337 | Me | 2 | Cl | CN | 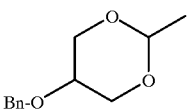 | 145–150 |
| 338 | Me | 2 | Cl | CN | 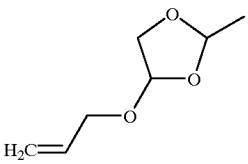 | Resin |
| 339 | Me | 2 | Cl | CN | 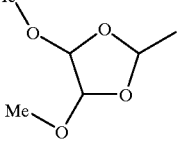 | Resin |
| 340 | Me | 2 | Cl | CN | 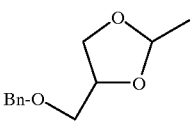 | Resin |
| 341 | Me | 2 | Cl | CN | 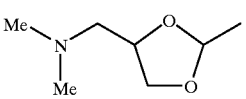 | Resin |
| 342 | Me | 2 | Cl | CN | 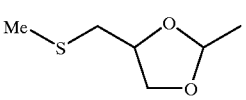 | Resin |

TABLE-continued
Compounds of the formula (I) according to the invention
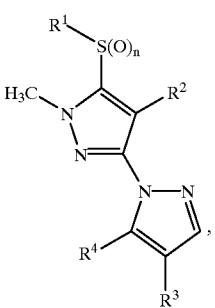
(I)
| No. | R¹ | n | R² | R³ | R⁴ | m.p. [° C.] or r.i. |
|---|---|---|---|---|---|---|
| 343 | Me | 2 | Cl | CN | 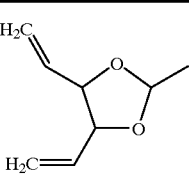 | Resin |
| 344 | Me | 2 | Cl | CN | 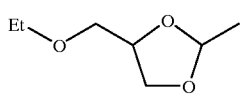 | Resin |
| 345 | Me | 2 | Cl | CN | 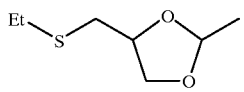 | Resin |
| 346 | Me | 2 | Cl | CN | 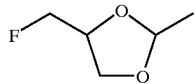 | Resin |
| 347 | Me | 2 | Cl | CN | 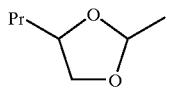 | Resin |
| 348 | Me | 2 | Cl | CN | 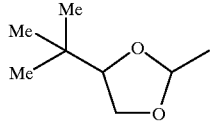 | Resin |
| 349 | Me | 2 | Cl | CN | 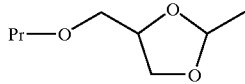 | Resin |
| 350 | Me | 2 | Br | CN | 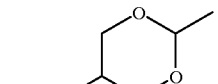 | Resin |
| 351 | Me | 2 | Br | CN | 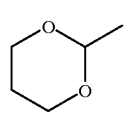 | 204–205 |

TABLE-continued
Compounds of the formula (I) according to the invention
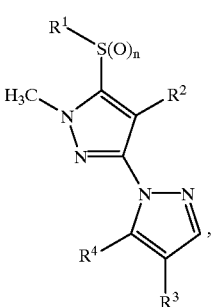
(I)
| No. | R¹ | n | R² | R³ | R⁴ | m.p. [° C.] or r.i. |
|---|---|---|---|---|---|---|
| 352 | Me | 2 | Br | CN | 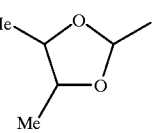 | 136–137 |
| 353 | Me | 2 | Br | CN | 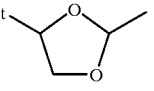 | 120–121 |
| 354 | Me | 2 | Br | CN | 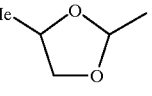 | Resin |
| 355 | Me | 2 | Br | CN | 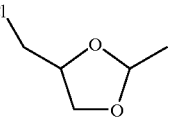 | Resin |
| 356 | Me | 2 | Br | CN | 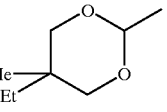 | 140–141 |
| 357 | Me | 2 | Br | CN | 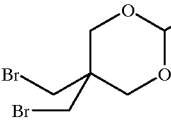 | 165–166 |
| 358 | Me | 2 | Br | CN | 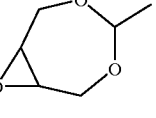 | |
| 359 | Me | 2 | Br | CN | 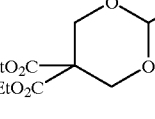 | Resin |
| 360 | Me | 2 | Iod | CN | 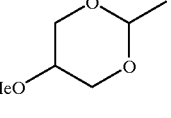 | Resin |

TABLE-continued

Compounds of the formula (I) according to the invention

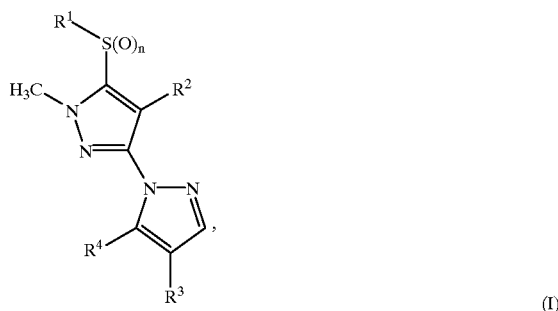

(I)

| No. | R¹ | n | R² | R³ | R⁴ | m.p. [° C.] or r.i. |
|---|---|---|---|---|---|---|
| 361 | Me | 2 | Iod | CN | 2-methyl-1,3-dioxane | Resin |
| 362 | Me | 2 | Iod | CN | 2,5,5-trimethyl-1,3-dioxane | Resin |
| 363 | Me | 2 | Iod | CN | 2,4-dimethyl-1,3-dioxane | Resin |
| 364 | Me | 2 | Iod | CN | 5-methoxy-2-methyl-1,3-dioxane | Resin |
| 365 | Me | 2 | Iod | CN | 2-methyl-5-phenoxy-1,3-dioxane | Resin |
| 366 | Me | 2 | Iod | CN | 2-methyl-1,3-dioxepane | Resin |
| 367 | Me | 2 | Iod | CN | 2-methyl-4,7-dihydro-1,3-dioxepine | Resin |
| 368 | Me | 2 | Iod | CN | 2,4-dimethyl-1,3-dioxepane | Resin |

TABLE-continued

Compounds of the formula (I) according to the invention

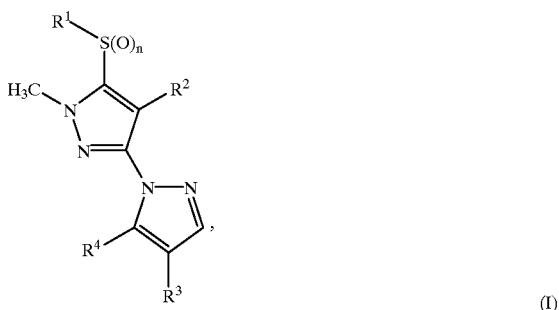

(I)

| No. | R¹ | n | R² | R³ | R⁴ | m.p. [° C.] or r.i. |
|---|---|---|---|---|---|---|
| 369 | Me | 2 | Iod | CN | 1,3-dioxolan-2-yl (Me) | Resin |
| 370 | Me | 2 | Iod | CN | 4,4,5,5-tetramethyl-1,3-dioxolan-2-yl (Me) | Resin |
| 371 | Me | 0 | Iod | CN | 5-methoxy-1,3-dioxan-2-yl (Me) | Resin |
| 372 | Me | 0 | Iod | CN | 1,3-dioxan-2-yl (Me) | Resin |
| 373 | Me | 0 | Iod | CN | 5,5-dimethyl-1,3-dioxan-2-yl (Me) | Resin |
| 374 | Me | 0 | Iod | CN | 4-methyl-1,3-dioxan-2-yl (Me) | Resin |
| 375 | Me | 0 | Iod | CN | 5-methoxy-1,3-dioxan-2-yl (Me) | Resin |
| 376 | Me | 0 | Iod | CN | 5-phenoxy-1,3-dioxan-2-yl (Me) | Resin |

TABLE-continued
Compounds of the formula (I) according to the invention
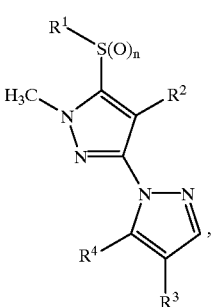
| No. | R¹ | n | R² | R³ | R⁴ | m.p. [° C.] or r.i. |
|---|---|---|---|---|---|---|
| 377 | Me | 0 | Iod | CN | 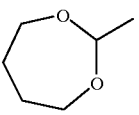 | Resin |
| 378 | Me | 0 | Iod | CN | 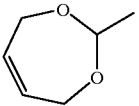 | Resin |
| 379 | Me | 0 | Iod | CN | 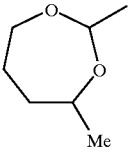 | Resin |
| 380 | Me | 0 | Iod | CN | 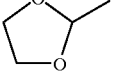 | Resin |
| 381 | Me | 0 | Iod | CN | 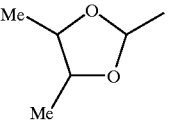 | Resin |
| 382 | Me | 0 | Iod | CN | 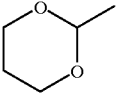 | Resin |
| 383 | Me | 1 | Iod | CN | 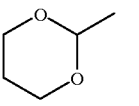 | Resin |
| 384 | Me | 1 | Iod | CN | 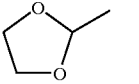 | Resin |
| 385 | Me | 0 | Cl | CN | CH=CHCO₂Me | Resin |
| 386 | Me | 0 | Br | CN | CH=CHCO₂Me | Resin |
| 387 | Me | 1 | Br | CN | CH=CHCO₂Me | 156–157 |
| 388 | Me | 0 | Cl | CN | CH=CHCO₂Pr | Resin |
| 389 | Me | 0 | Cl | CN | CH=CHCO₂Pr | Resin |
| 390 | Me | 0 | Cl | CN | CH=CHCO₂Bu | Resin |

TABLE-continued

Compounds of the formula (I) according to the invention

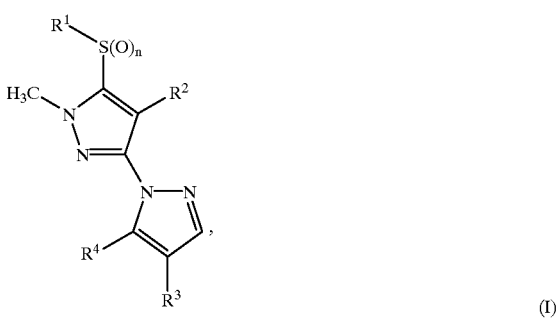

(I)

| No. | R$^1$ | n | R$^2$ | R$^3$ | R$^4$ | m.p. [° C.] or r.i. |
|---|---|---|---|---|---|---|
| 391 | Me | 0 | Cl | CN | CH=CHCO$_2$-n-Pentyl | Resin |
| 392 | Me | 0 | Cl | CN | CH=CHCO$_2$-n-Hexyl | Resin |
| 393 | Me | 0 | Cl | CN | CH=CHCO$_2$H | Resin |
| 394 | Me | 0 | Br | CN | CH=CHCO$_2$Pr | Resin |
| 395 | Me | 0 | Br | CN | CH=CHCO$_2$Pr | Resin |
| 396 | Me | 2 | Br | CN | CH=CHCO$_2$Pr | Resin |
| 397 | Me | 2 | Br | CN | CH=CHCO$_2$Bu | Resin |
| 398 | Me | 2 | Br | CN | CH=CClCO$_2$Bu | Resin |
| 399 | Me | 2 | Br | CN | CH=CClCO$_2$Pr | Resin |
| 400 | Me | 0 | Br | CN | CH$_2$—CHClCO$_2$Et | Resin |
| 401 | Me | 2 | Br | CN | CH=CClCO$_2$-i-Pr | Resin |
| 402 | Me | 2 | Cl | CN | CH(OH)Me | Resin |
| 403 | Me | 0 | Cl | CN | CH(OMe)Me | Resin |
| 404 | Me | 0 | Br | CN | CH(OMe)Me | Resin |
| 405 | Me | 2 | Cl | CN | CH(OMe)Me | Resin |
| 406 | Me | 0 | Cl | CN | CH(OH)Me | Resin |
| 407 | Me | 2 | Br | CN | CH(OH)Me | 139–140 |
| 408 | Me | 0 | Cl | CN | CH(F)Me | Resin |
| 409 | Me | 0 | Br | CN | CH(F)Me | Resin |

TABLE-continued
Compounds of the formula (I) according to the invention
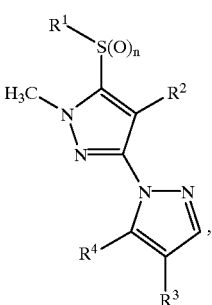
| No. | R¹ | n | R² | R³ | R⁴ | m.p. [° C.] or r.i. |
|---|---|---|---|---|---|---|
| 410 | Me | 2 | Cl | CN |  | Resin |
| 411 | Me | 1 | Cl | NO₂ | —CHO | Viscous oil |
| 412 | Me | 0 | Cl | NO₂ | —CHO | Viscous oil |
| 413 | Me | 0 | Cl | NO₂ | CH(OMe)₂ | 59–61 |
| 414 | Me | 2 | Cl | NO₂ | CH(OEt)₂ | Resin |
| 415 | Me | 2 | Br | NO₂ | CH(OMe)₂ | Resin |
| 416 | Me | 0 | Cl | NO₂ | 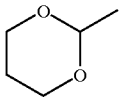 | Resin |
| 417 | Me | 0 | Br | NO₂ | 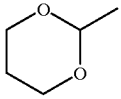 | Resin |
| 418 | Me | 2 | Br | NO₂ | 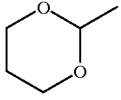 | Resin |
| 419 | Me | 1 | Br | NO₂ | 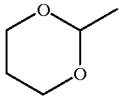 | Resin |
| 420 | Me | 0 | Cl | NO₂ | 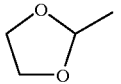 | Resin |
| 421 | Me | 0 | Br | NO₂ | 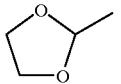 | Resin |
| 422 | Me | 2 | Br | NO₂ | 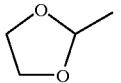 | Resin |
| 423 | Me | 1 | Br | NO₂ | 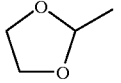 | Resin |

TABLE-continued

Compounds of the formula (I) according to the invention

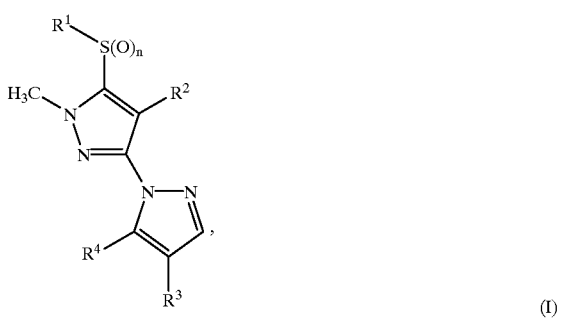

(I)

| No. | R¹ | n | R² | R³ | R⁴ | m.p. [° C.] or r.i. |
|---|---|---|---|---|---|---|
| 424 | Me | 2 | Cl | CN | NH₂ | 245–248 |
| 425 | Me | 2 | Cl | CN | (tetrahydrofuran-2-yl)methyl-NH- | 182–184 |
| 426 | Me | 2 | Cl | CN | NHCH₂CH₂OMe | 150–152 |
| 427 | Me | 2 | Cl | CN | HC≡C-CH₂-N(Me)- | 122–123 |
| 428 | Me | 2 | CN | CN | NH₂ | 300 |
| 429 | Me | 2 | Cl | CN | (MeO)₂CH-CH(Me)-NH- | 124–126 |
| 430 | Me | 2 | Cl | CN | (1,3-dioxolan-2-yl)-NH- | 148–150 |
| 431 | Me | 1 | Cl | CN | NH₂ | 171–173 |
| 432 | Me | 1 | Cl | NO₂ | NH₂ | |
| 433 | Me | 0 | Cl | NO₂ | NH₂ | 148–151 |
| 434 | Me | 0 | Cl | C(=S)NH₂ | NH₂ | 159–162 |
| 435 | Me | 2 | Cl | CN | (4R)-4-methyl-2-methyl-1,3-dioxane | Resin |
| 436 | Me | 2 | Cl | CN | (4S)-4-methyl-2-methyl-1,3-dioxane | Resin |
| 437 | Me | 2 | Cl | CN | (4,6-meso)-4,6-dimethyl-2-methyl-1,3-dioxane | Resin |

TABLE-continued
Compounds of the formula (I) according to the invention
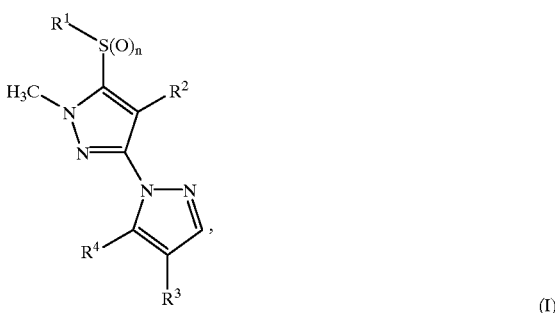
(I)
| No. | R¹ | n | R² | R³ | R⁴ | m.p. [° C.] or r.i. |
|---|---|---|---|---|---|---|
| 438 | Me | 2 | Cl | CN | (4R,6R)-configuration 4,6-dimethyl-1,3-dioxan-2-yl | Resin |
| 439 | Me | 2 | Cl | CN | (4S,6S)-configuration 4,6-dimethyl-1,3-dioxan-2-yl | Resin |
| 440 | Me | 2 | Cl | CN | NH(C=O)CH₂OMe | 194–195 |
| 441 | Me | 0 | F | CN | 2-methyl-1,3-dioxan-2-yl | |
| 442 | Me | 0 | F | CN | CH(OEt)₂ | |
| 443 | Me | 2 | F | CN | 2-methyl-1,3-dioxan-2-yl | |
| 444 | Me | 2 | F | CN | CH(OEt)₂ | |
| 445 | Me | 2 | F | CN | 2,5,5-trimethyl-1,3-dioxan-2-yl | |
| 446 | Me | 2 | F | CN | 2,4-dimethyl-1,3-dioxan-2-yl | |

C. Biological Examples

C.1 Pre-Emergence

Seeds or rhizome pieces of monocotyledonous or dicotyledonous harmful and useful plants are placed in sandy loam soil in little pots having a diameter of 9 cm and covered with soil. Alteratively, for the rice test rice plants and harmful plants which are undesired in this crop of useful plants are cultivated in soil which is supersaturated with water. The compositions according to the invention, formulated as emulsifiable concentrates, are then applied to the surface of the soil cover as emulsions in a volume of water of 800 l/ha (converted), in various dosages, or, in the rice test, poured into the irrigation water. The pots are subsequently kept in a greenhouse under optimum conditions to cultivate the plants further. The damage to the useful and the harmful plants is rated visually after the emergence of these plants, i.e. approximately 2 to 4 weeks after the start of the test.

At an application rate of 330 g/ha, for example the compounds Nos. 39, 50, 75 and 84 exhibited a 90 to 100% effect against *Setaria viridis*. At the same application rate, for example the compounds Nos. 39, 50, 66 and 80 exhibited a 90 to 100% effect against *Stellaria media*.

At an application rate of 80 g/ha, for example the compounds Nos. 12 and 32 exhibited a 100% effect against *Matricaria inodora*, *Chenopodium album* and *Veronica persica*.

At an application rate of 80 g/ha, for example the compounds Nos. 12, 32 and 105 caused no damage in rice.

Moreover, at an application rate of less than 1000 g/ha the compounds Nos. 14, 15, 24, 28, 32, 39, 111, 145, 146, 156, 163, 166, 213, 242, 244, 246, 247, 252, 285, 313, 317, 319, 325, 342, 349, 350, 354, 374, 437 and 438 exhibited a 90 to 100% effect against various mono- and dicotyledonous weeds.

C.2 Post-Emergence

Useful plants and different weeds or grasses were grown on sandy loam soil in paper pots having a diameter of 9 cm in a greenhouse until they had reached a growth stage of 3–4 leaves and then treated with a water-diluted formulation of the compounds according to the invention, an amount of water of 300 l/ha being applied. Four weeks after the treatment, the plants were rated visually for any kind of damage by the active compounds applied, taking into account in particular the extent of lasting impairment of growth. Evaluation was carried out using a percent scale (0–100%), by comparison with the untreated control.

At an application rate of 330 g/ha, for example the compounds Nos. 39, 50, 75 and 80 exhibited a 90 to 100% effect against *Amaranthus retroflexus*. At the same application rate, for example the compounds Nos. 39 and 80 exhibited a 90 to 100% effect against *Setaria viridis*.

At an application rate of 80 g/ha, for example the compounds Nos. 12, 32 and 122 exhibited an 80 to 100% effect against *Galium aparine* and *Fallopia convolvulus*. At the same application rate, for example the compounds Nos. 12, 32, 39, 75 and 105 exhibited a 100% effect against *Pharbitis purpurea*.

At an application rate of 80 g/ha, for example the compounds Nos. 110 and 119 caused no damage in corn. At the same application rate, for example the compounds Nos. 105 and 110 caused no damage in rice.

Moreover, at an application rate of less than 1000 g/ha the compounds Nos. 14, 15, 24, 28, 32, 36, 39, 89, 111, 145, 146, 156, 163, 180, 202, 208, 212, 215, 216, 220, 229, 247, 304, 305, 312, 313, 315, 322, 349, 351, 352, 353, 437 and 438 exhibited a 90 to 100 % effect against various mono- and dicotyledonous weeds.

What is claimed is:

1. A 1-methyl-5-alkylsulfonyl-substituted pyrazolylpyrazole of the formula (I)

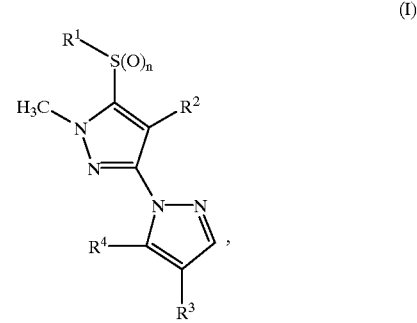

in which $R^1$ is $C_1$–$C_3$-alkyl, $C_3$–$C_8$-cycloalkyl or $C_2$–$C_3$-alkenyl, where these radicals are unsubstituted or substituted by one or more identical or different halogen atoms;

$R^2$ is halogen or cyano;

$R^3$ is cyano, nitro or thiocarbamoyl;

$R^4$ is

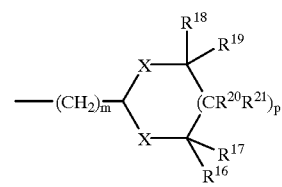

where $R^{16}$, $R^{17}$, $R^{18}$, $R^{19}$, $R^{20}$ and $R^{21}$ independently of one another are hydrogen, $C_1$–$C_4$-alkyl which is unsubstituted or substituted by one or more identical or different halogen atoms, or two of these radicals together form a bond;

x is oxygen or sulfur, m is 0, 1 or 2, and p is 0, 1 or 2; and n is 2.

2. The pyrazolylpyrazole of the formula (I) as claimed in claim 1 in which $R^1$ is $C_1$–$C_3$-alkyl or $C_3$–$C_6$-cycloalkyl, which are optionally substituted by one or more identical or different halogen atoms from the group consisting of chlorine and fluorine and $R^2$ is bromine, chlorine or cyano.

3. The pyrazolylpyrazole of the formula (I) as claimed in claim 1 in which $R^1$ is $C_1$–$C_3$-alkyl or $C_3$–$C_6$-cycloalkyl.

4. The pyrazolylpyrazole of the formula (I) as claimed in claim 1 in which $R^1$ is methyl, ethyl, propyl, isopropyl or cyclopropyl;

$R^3$ is cyano or nitro.

5. The pyrazolylpyrazole of the formula (I) as claimed in claim 1 in which $R^1$ is methyl or cyclopropyl; and $R^2$ is chlorine or bromine.

6. The pyrazolylpyrazole of the formula (I) as claimed in claim 1 in which $R^1$ is $C_1$–$C_3$-alkyl, $C_3$–$C_8$-cycloalkyl or $C_2$–$C_3$-alkenyl, where these radicals are unsubstituted or substituted by one or more identical or different halogen atoms from the group consisting of chlorine and fluorine and $R^2$ is bromine, chlorine, fluorine or cyano.

7. A herbicidal composition, which comprises at least one compound of the formula (I) according to claim 1.

8. The herbicidal composition as claimed in claim 7 in a mixture with formulation auxiliaries.

9. A method for controlling undesirable plants, which comprises applying an effective amount of at least one compound of the formula (I) as claimed in claim 1 on the plants or on the location of the undesirable plant growth.

10. The pyrazolylpyrazole as claimed in claim 1, wherein $R^3$ is cyano or nitro.

11. The pyrazolylpyrazole as claimed in claimed in claim 1, wherein X is oxygen.

12. The pyrazolylpyrazole as claimed in claimed in claim 1 which is

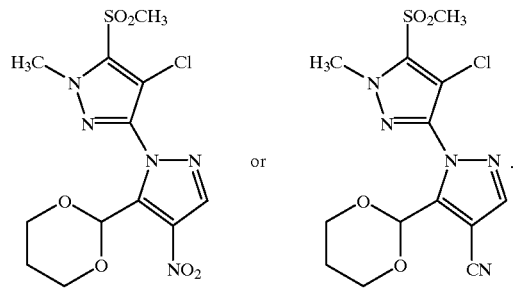

13. The pyrazolylpyrazole as claimed in claim 1 which is

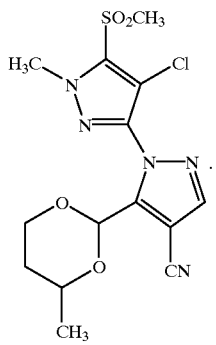

14. The method as claimed in claim 9, wherein the undesirable plants are in a crop of useful plants.

15. The method according to claim 14, where the useful plants are transgenic plants.

* * * * *